United States Patent
Mizutani et al.

(10) Patent No.: US 8,201,607 B2
(45) Date of Patent: Jun. 19, 2012

(54) SANITARY ABSORPTIVE ARTICLE PRODUCING DEVICE AND METHOD

(75) Inventors: Satoshi Mizutani, Kanonji (JP); Masashi Hosokawa, Kanonjishi (JP); Koichi Yamaki, Kanonji (JP); Yuki Noda, Kanonji (JP)

(73) Assignee: Uni-Charm Corporation, Kawanoe-Shi (JP)

(*) Notice: Subject to any disclaimer, the term of this patent is extended or adjusted under 35 U.S.C. 154(b) by 239 days.

(21) Appl. No.: 12/496,779

(22) Filed: Jul. 2, 2009

(65) Prior Publication Data
US 2009/0266491 A1 Oct. 29, 2009

Related U.S. Application Data

(60) Division of application No. 11/068,532, filed on Feb. 28, 2005, now Pat. No. 7,591,809, which is a continuation of application No. PCT/JP03/11066, filed on Aug. 29, 2003.

(30) Foreign Application Priority Data

Aug. 30, 2002 (JP) .................. 2002-253331

(51) Int. Cl.
*B32B 37/00* (2006.01)
*B32B 37/02* (2006.01)
*B32B 38/00* (2006.01)
*B32B 38/04* (2006.01)
*B32B 38/10* (2006.01)

(52) U.S. Cl. ........ 156/519; 156/250; 156/252; 156/253; 156/256; 156/510; 156/516; 156/517

(58) Field of Classification Search ............ 156/250, 156/252, 253, 256, 510, 516, 517, 519; 604/366, 604/385.17, 385.201
See application file for complete search history.

(56) References Cited

U.S. PATENT DOCUMENTS
1,982,005 A 11/1934 Hutter
(Continued)

FOREIGN PATENT DOCUMENTS
CN 1307462 A 8/2001
(Continued)

OTHER PUBLICATIONS
International Search Report dated Nov. 25, 2003 issued for corresponding Application No. PCT/JP03/11066.

*Primary Examiner* — Mark A Osele
*Assistant Examiner* — Christopher C Caillouet
(74) *Attorney, Agent, or Firm* — Morrison & Foerster LLP

(57) ABSTRACT

A sanitary absorptive article producing device and method, particularly suitable for producing interlabial pads, which are small-sized sanitary absorptive articles having a mini-sheet piece. The method comprises a main-section assembly step for disposing an absorptive body between a face-side sheet continuous-member and a back-side sheet continuous-member, joining the face-side sheet continuous-member to the back-side sheet continuous-member to form a main-section continuous-body having a portion continuous therewith which becomes the main section of the sanitary absorptive article, and a mini-sheet assembly step for joining the mini-sheet piece to the back-side sheet continuous-member of the main-section continuous-body to form a sanitary absorptive continuous-body. The sanitary absorptive article continuous-bodies have their unnecessary potions removed by a round-cutting step to become individual sanitary absorptive articles.

9 Claims, 18 Drawing Sheets

U.S. PATENT DOCUMENTS

| | | | |
|---|---|---|---|
| 3,201,295 | A | 8/1965 | De Woskin |
| 3,289,254 | A | 12/1966 | Joa |
| 3,445,897 | A | 5/1969 | Franz |
| 3,629,039 | A | 12/1971 | Frick |
| 3,746,592 | A | 7/1973 | Nystrand et al. |
| 3,814,100 | A | 6/1974 | Nystrand et al. |
| 3,844,288 | A | 10/1974 | Kiela |
| 3,913,578 | A | 10/1975 | Schaar |
| 4,069,822 | A | 1/1978 | Buell |
| 4,595,392 | A | 6/1986 | Johnson et al. |
| 4,595,932 | A | 6/1986 | Ruhl et al. |
| 4,650,530 | A | 3/1987 | Mahoney et al. |
| 4,842,666 | A | 6/1989 | Werenicz et al. |
| 4,900,377 | A * | 2/1990 | Redford et al. ............... 156/62.2 |
| 5,344,516 | A | 9/1994 | Tanji et al. |
| 5,453,143 | A | 9/1995 | Menard |
| 5,567,260 | A | 10/1996 | McFall |
| 5,643,396 | A | 7/1997 | Rajala et al. |
| 5,711,832 | A | 1/1998 | Glaug et al. |
| 5,743,994 | A * | 4/1998 | Roessler et al. ............... 156/495 |
| 5,792,131 | A | 8/1998 | Mizutani et al. |
| 5,868,727 | A | 2/1999 | Barr et al. |
| 5,891,126 | A | 4/1999 | Osborn, III et al. |
| 5,916,205 | A | 6/1999 | Olson et al. |
| 5,928,452 | A | 7/1999 | McFall et al. |
| 6,093,474 | A | 7/2000 | Sironi et al. |
| 6,131,575 | A | 10/2000 | Lenker et al. |
| 6,183,456 | B1 | 2/2001 | Brown et al. |
| 6,183,587 | B1 | 2/2001 | McFall et al. |
| 6,210,385 | B1 | 4/2001 | Mizutani |
| 6,210,386 | B1 | 4/2001 | Inoue et al. |
| 6,250,357 | B1 | 6/2001 | Niedermeyer |
| 6,355,022 | B1 | 3/2002 | Osborn, III et al. |
| 6,503,233 | B1 * | 1/2003 | Chen et al. ............... 604/385.01 |
| 6,596,113 | B2 | 7/2003 | Csida et al. |
| 6,635,136 | B2 | 10/2003 | White et al. |
| 7,074,214 | B2 | 7/2006 | Mizutani et al. |
| 2001/0000796 | A1 | 5/2001 | Osborn et al. |
| 2002/0010449 | A1 | 1/2002 | Mizutani |
| 2002/0022108 | A1 * | 2/2002 | Krantz et al. ................. 428/100 |
| 2003/0093054 | A1 | 5/2003 | Sierri et al. |
| 2004/0147894 | A1 | 7/2004 | Mizutani et al. |
| 2004/0147898 | A1 | 7/2004 | Mizutani et al. |

FOREIGN PATENT DOCUMENTS

| | | | |
|---|---|---|---|
| CN | 1307462 | A | 8/2001 |
| CN | 1371265 | A | 9/2002 |
| CN | 1371265 | A | 9/2002 |
| EP | 888764 | | 1/1999 |
| JP | 49003722 | | 1/1974 |
| JP | 61-108258 | | 7/1986 |
| JP | 63-260556 | | 10/1988 |
| JP | 03-037062 | A1 | 2/1991 |
| JP | 03-037062 | A1 | 2/1991 |
| JP | 03056366 | | 3/1991 |
| JP | 5-237151 | | 9/1993 |
| JP | 05-293138 | A1 | 11/1993 |
| JP | 05-293138 | A1 | 11/1993 |
| JP | 06506368 | | 7/1994 |
| JP | 0640203 | | 10/1994 |
| JP | 07-024007 | A1 | 1/1995 |
| JP | 07-024007 | A1 | 1/1995 |
| JP | 08-117273 | A1 | 5/1996 |
| JP | 08-117273 | A1 | 5/1996 |
| JP | 08-215242 | A1 | 8/1996 |
| JP | 08-215242 | A1 | 8/1996 |
| JP | 08215242 | | 8/1996 |
| JP | 08-511707 | A1 | 12/1996 |
| JP | 08-511707 | A1 | 12/1996 |
| JP | 09-000567 | A1 | 1/1997 |
| JP | 09-000567 | A1 | 1/1997 |
| JP | 2000-051267 | A | 2/2000 |
| JP | 0051267 | | 2/2000 |
| JP | 2001-095845 | A1 | 4/2001 |
| JP | 2001-095845 | A1 | 4/2001 |
| JP | 2001509402 | | 7/2001 |
| JP | 2002-513633 | A1 | 5/2002 |
| JP | 2002-513633 | A1 | 5/2002 |
| JP | 2002-513638 | A1 | 5/2002 |
| JP | 2002-513638 | A1 | 5/2002 |
| JP | 02513633 | | 5/2002 |
| JP | 2002534163 | | 10/2002 |
| WO | 9211825 | | 7/1992 |
| WO | WO-9211825 | | 7/1992 |
| WO | 95/00094 | | 1/1995 |
| WO | 9500094 | | 1/1995 |
| WO | WO-95/00094 | | 1/1995 |
| WO | WO-9500094 | | 1/1995 |
| WO | 95/17148 | A2 | 6/1995 |
| WO | WO-95/17148 | A2 | 6/1995 |
| WO | 99/26578 | A1 | 6/1999 |
| WO | 99/26770 | A2 | 6/1999 |
| WO | WO-99/26578 | A1 | 6/1999 |
| WO | WO-99/26770 | A2 | 6/1999 |
| WO | 99-56681 | | 11/1999 |
| WO | 9956681 | | 11/1999 |
| WO | 9956689 | | 11/1999 |
| WO | WO-99-56681 | | 11/1999 |
| WO | WO-9956681 | | 11/1999 |
| WO | WO-9956689 | | 11/1999 |
| WO | 0040192 | | 7/2000 |
| WO | WO-0040192 | | 7/2000 |
| WO | 01/47458 | | 7/2001 |
| WO | WO-01/47458 | | 7/2001 |
| WO | 02/094145 | A1 | 11/2002 |
| WO | WO-02/094145 | A1 | 11/2002 |

* cited by examiner

SANITARY ABSORPTIVE ARTICLE PRODUCING DEVICE AND METHOD

CROSS-REFERENCE TO RELATED APPLICATIONS

This application is a Divisional application of U.S. patent application Ser. No. 11/068,532 filed Feb. 28, 2005 which is a Continuation of International Application No. PCT/JP2003/11066 filed Aug. 29, 2003, which application published in Japanese on Mar. 25, 2004 as WO 2004/024046 A1 under PCT Article 21 (2). The International Application PCT/JP2003/11066 is based upon and claims the benefit of priority from Japanese Patent Application No. 2002-253331 filed on Aug. 30, 2002, the entire contents of which is incorporated herein by reference.

FIELD OF THE INVENTION

The present invention relates to a method for producing a sanitary absorbent article, an apparatus thereof and a sanitary absorbent article to be produced by the producing method and, especially, a method for producing an interlabial pad that can be worn easily between labia, an apparatus thereof, and an interlabial pad to be produced by the producing method.

RELATED ART

Conventionally, a sanitary napkin and a tampon are used generally as sanitary products for female. Here, there have been great efforts to prevent the leak of blood from a gap caused by poor adhesion near the ostium vaginae as for the sanitary napkin. Moreover, as for the tampon, great efforts have been made for relieving the foreign feeling, the discomfort, and the difficulty in inserting the tampon in vagina, which are caused by the nature of the product.

Under such situation, sanitary products of the interlabial pad have attracted people as a sanitary product positioned between the sanitary napkin and the tampon in recent years. The interlabial pad is used by inserting its portion between the labia and bringing into contact with the inner face of labia, it prevents the blood from leaking because of higher adhesion to the body than that of the sanitary napkin, and the blood from bringing widely into contact with the body by diffusing, so it is sanitary and clean. Moreover, the interlabial pad has characteristics that it excels in a feeling of wearing, is comfortable because of being smaller than the sanitary napkin, and has lower psychological resistance on wearing than that of the tampon which is inserted into the vagina.

By the way, a producing method for supplying a surface material and a back material in general, supplying an absorbent body in a way to enter between them, and bonding them is known, as a producing method of sanitary napkin. For instance, a producing method of a sanitary napkin provided further with an elastic body is disclosed in Laid-Open Japanese Patent Publication HEI 8-215242.

There is a drawback that parts that should installed three-dimensionally by folding the napkin and so on cannot be installed, though a flat napkin can be produced, in such a conventional producing method of sanitary napkin.

SUMMARY OF THE INVENTION

The present invention was devised in view of said inconvenience and, has an object of providing a method built-in with an installation process for parts that should be three-dimensionally installed, in a sanitary absorbent article, for producing integrally the sanitary absorbent article from a raw material by a series of processes, an apparatus thereof, and the sanitary absorbent article prepared by the method.

That is, a producing method of sanitary absorbent article for arranging an absorbent body between a surface side sheet and a back side sheet, and attaching a mini-sheet piece to the back side sheet, the method comprising steps of forming absorbent layer which is a main part of the sanitary absorbent article by arranging the absorbent body in a way to be fitted between a surface side sheet continuous member formed as a continuous member of the
surface side sheet and a back side sheet continuous member formed as a continuous member of the back side sheet, and at least after joining together the continuous surface side sheet member and the continuous back side sheet member, thereafter cutting off into each sanitary absorbent article by excising unnecessary portions. The producing method of sanitary absorbent article comprising the above steps, a producing apparatus thereof, and a sanitary absorbent article made the producing method shall be provided.

More specifically, the present invention provides followings.

(1) A method for producing a sanitary absorbent article having a surface side sheet, a back side sheet, an absorbent body arranged between the surface side sheet and the back side sheet, and a mini-sheet piece provided on the back side sheet, the method comprising: a main part assembly step of forming a main part continuous body by arranging said absorbent body between a surface side sheet continuous member and a back side sheet continuous member and joining said surface side sheet continuous member and said back side sheet continuous member; and a mini-sheet assembly step of forming a sanitary absorbent article continuous body by joining said back side sheet continuous member of said main part continuous body and said mini-sheet piece.

(2) The method can be modified, wherein both said joining of said main part assembly step and said joining of said mini-sheet assembly step is temporary joining; and the method further comprises a concurrent regular joining step of regularly joining said surface side sheet continuous member and said back side sheet continuous member and regularly joining said back side sheet continuous member and said mini-sheet piece at the same time.

(3) The method can further be modified, wherein said joining of said main part assembly step and said mini-sheet assembly step is regular joining.

(4) The method can be modified to further comprise a folding step of folding said main part continuous body or said sanitary absorbent article continuous body at a center crease provided along a direction where said main part continuous body or said sanitary absorbent article continuous body is continuous.

(5) The said folding step further comprises a step of folding said main part continuous body along a pair of side creases which are substantially line-symmetry with respect to said center crease.

(6) The method can further be modified, wherein; in said folding step, said main part continuous body is folded along said center crease such that said back side sheet continuous member becomes inside, and said main part continuous body is folded along said pair of side creases such that said back side sheet continuous member becomes outside.

(7) The method can be modified to further comprise a side creases releasing step of restoring a portion folded along said side creases.

(8) The method can be modified to further comprise a round cut step of producing each sanitary absorbent article by cutting off said sanitary absorbent article continuous body in a state where said sanitary absorbent article continuous body is folded along the center crease.

(9) An apparatus for producing a sanitary absorbent article having: a surface side sheet, a back side sheet, an absorbent body arranged between the surface side sheet and the back side sheet, and a mini-sheet piece provided on the back side sheet, said apparatus comprising: a main part assembly unit having: a mechanism of supplying a surface side sheet continuous member, a mechanism of supplying a back side sheet continuous member, a mechanism of supplying an absorbent body which arranges the absorbent body between the surface side sheet continuous member and the back side sheet continuous member, and a mechanism of assembling a main part continuous body which forms a main part continuous body by joining said surface side sheet continuous member and said back side sheet continuous member, a mini-sheet assembly unit having: a mechanism of supplying a mini-sheet piece which arranges a mini-sheet piece on said back side sheet continuous member of said main part continuous body, and a mechanism of attaching a mini-sheet which forms a sanitary absorbent article continuous body by joining said back side sheet continuous member and said mini-sheet piece.

(10) The apparatus can further be modified, wherein: said mechanism of supplying a surface side sheet continuous member comprises: a first rolling roller for rolling a raw fabric roll of surface side sheet, a first drawing roller for drawing said raw fabric roll of surface side sheet, said mechanism of supplying a back side sheet continuous member comprises: a second rolling roller for rolling a raw fabric roll of back side sheet, a second drawing roller for drawing said raw fabric roll of back side sheet, said mechanism of supplying a mini-sheet piece comprises: a third rolling roller for rolling a raw fabric roll of mini-sheet, a third drawing roller for drawing said raw fabric roll of mini-sheet, said mechanism of attaching a mini-sheet comprises: a plurality of first feeding rollers, and a suction roller.

(11) The apparatus can further comprise a concurrent regular joining unit for regularly joining at least said surface side sheet continuous member and said back side sheet continuous member at the same time regularly joining said back side sheet continuous member and said mini-sheet piece.

(12) The said concurrent regular joining unit can comprise a concurrent regular joining upper roller and a concurrent regular joining lower roller.

(13) The apparatus can further comprise a folding unit for folding said main part continuous body or said sanitary absorbent article continuous body at a center crease along a direction where said main part continuous body or said sanitary absorbent article continuous body is continuous.

(14) The folding unit can comprise a plurality of second feeding rollers.

(15) The apparatus can further comprise a round cut unit of cutting off said sanitary absorbent article continuous body in a state where said sanitary absorbent article continuous body is folded along said center crease.

(16) The said round cut unit can comprise a cutter roller having a cutter blade.

(17) A sanitary absorbent article can be produced by the disclosed methods.

BRIEF DESCRIPTION OF THE DRAWINGS

FIG. 25A is seen from the side.

DESCRIPTION OF THE PREFERRED EMBODIMENT

Figure 1:
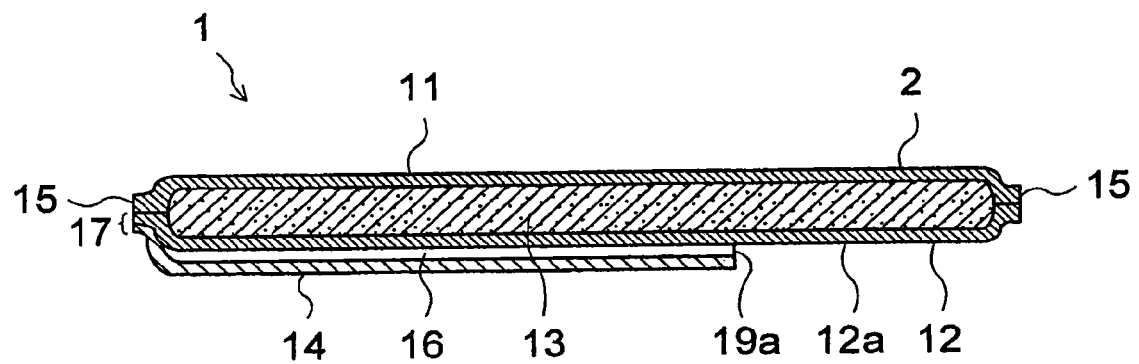
FIG. 1 is a cross section view in the longitudinal direction where an internal element of an interlabial pad according to one embodiment of the present invention is shown.

Hereinafter, embodiments of the present invention shall be described referring to drawings; however, one embodiment of the interlabial pad produced by the producing apparatus shall be described, before describing the apparatus for producing interlabial pad according to the present inventions. That is, the present invention relates to how to mass-produce the interlabial pad as described below.

It should be appreciated that the same symbol in the drawing indicates the same member.

Basic Structure of the Interlabial Pad

Figure 2:
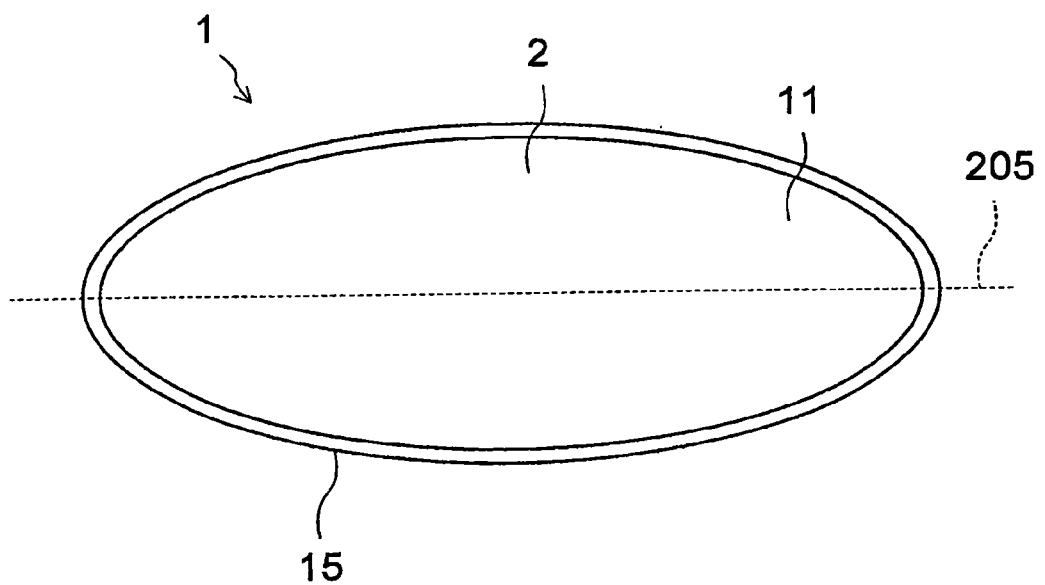
FIG. 2 is a plan view where the body side face of the interlabial pad of FIG. 1 is shown.
Figure 3:
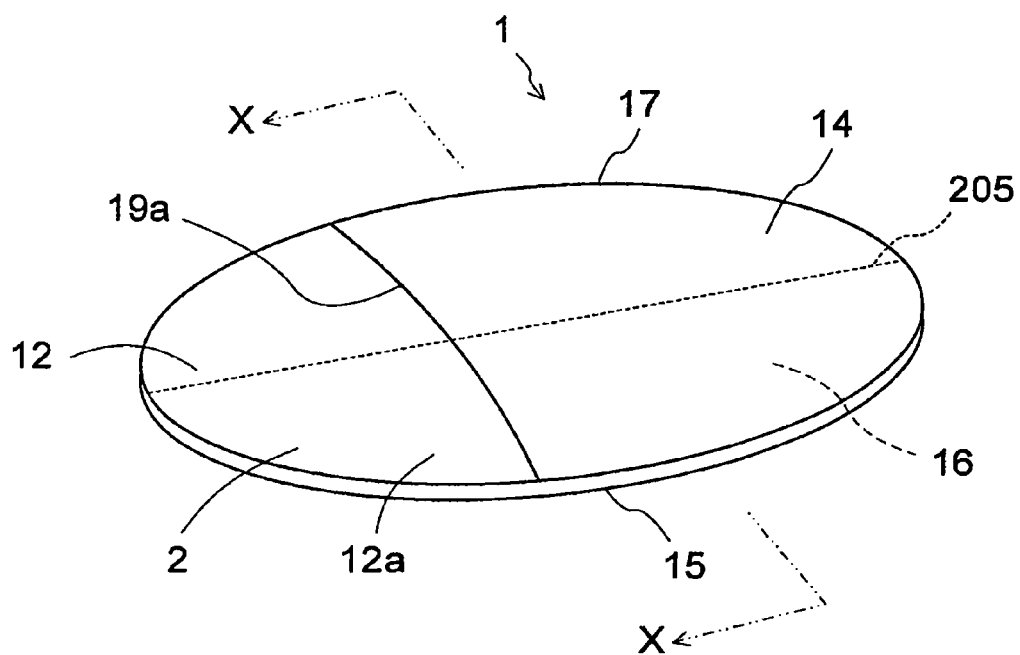
FIG. 3 is an perspective view where the opposite body side face to body side face of the interlabial pad of FIG. 1 is shown.
Figure 4:
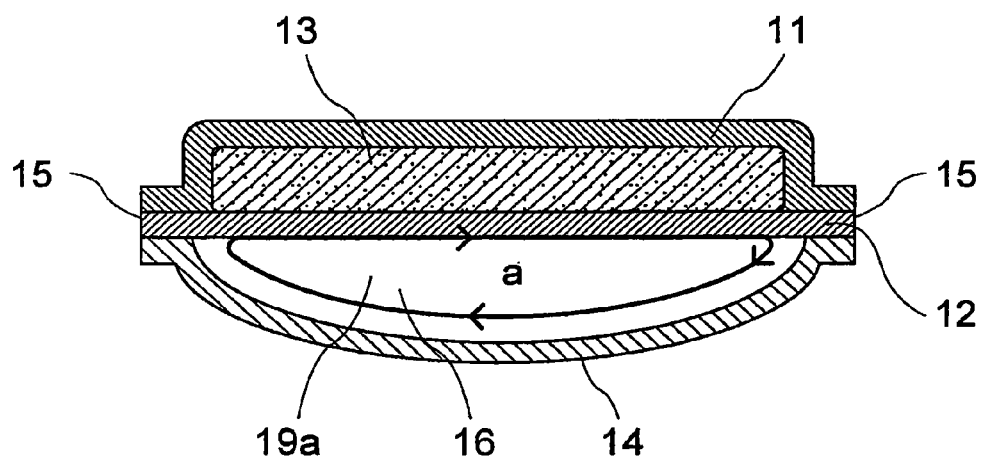
FIG. 4 is a cross section view of the X-X section in FIG. 3.

FIG. 1 is a cross section in the longitudinal direction where the elements of an interlabial 1 to be produced by the present invention is shown. FIG. 2 is a plan view of the interlabial pad 1 of FIG. 1, and shows the body side face of the interlabial pad 1. FIG. 3 is an perspective view of the interlabial pad 1, and shows the opposite body side face to body side face of the interlabial pad 1. FIG. 4 is a cross section view of the X-X section in FIG. 3.

As shown in FIG. 1, the interlabial pad 1 has a surface side sheet 11 (body side) of water permeable material and a back side sheet 12 (opposite side to the body side) of water impermeable material, and the absorbent body 13. As for the surface side sheet 11 and the back side sheet 12, at least the surface side sheet 11 and the back side sheet 12 are joined in a joint part 15 installed on the surrounding edge of an absorbent body 13 to enclose the absorbent body 13, and constitute an integrally formed absorbent layer 2. The joint of the surface side sheet 11 and the back side sheet 12 is interlaid by the melted type bonding by the heat emboss and/or hot melt type adhesive. Moreover, to prevent the separation between layers against the surface side sheet 11 and the back side sheet 12, the absorbent body 13 is joined at least to either of them.

Here, "join" means to make two or more elements fixed by using any of means such as adhesive, connecting and so on. "Join" includes "temporary join" and "regular join", and "temporary join" means to fix two or more elements temporarily before fix them tightly, while "regular join" means to fix two or more elements tightly after temporary joining.

It is also possible to prevent the aforementioned separation between layers by joining the surface side sheet 11 and the back side sheet 12 in the inner edge part except for the joint part 15. Moreover, the separation between layers is caused easily when the layers are wet, and the heat emboss type bonding is more desirable to prevent the separation. The heat emboss type bonding can be used without limitation, in the pattern of a dot pattern or a screen pattern. The wet strength can be conserved without disturbing the liquid penetration, by joining in the range of 3 to 20% in emboss area rate.

On the opposite body side face to body side face 12a of the back side sheet 12, a mini-sheet piece 14 that covers about two thirds of the back side sheet 12 area is joined with the back side sheet 12 in the mini-sheet joint part 17 except for a finger insertion opening 19a, and a pocket 16 is formed, as shown in FIG. 1 and FIG. 3. Concretely, the length in the longitudinal direction of the mini-sheet piece 14 is about 55 mm while the length in the longitudinal direction of the absorbent layer 2 is 85 mm, and the back side sheet 12 will have an area not covered with the mini-sheet piece 14 in the range of about 30 mm in the longitudinal direction.

FIG. 2 is the plan view where the body side face of the interlabial pad 1 is shown, and the broken line 205 indicates the center crease.

Moreover, FIG. 4 is a cross view section where the X-X section of FIG. 3 is shown, and the inner total peripheral length of the finger insertion opening shown the hemicycle arrow line a is about 40 mm, in this embodiment.

As FIG. 4 is a schematic cross section view, the size relation of each structure is different from the actual for the convenience of the explanation, for instance, the thickness of the joint part 15 and so on described later are greatly different from the actual size.

FIG. 5A to FIG. 5D are schematic cross section views where the section in the lateral direction of the interlabial pad 1 in the state before individual interlabial pads 1 are cut off from a sanitary absorbent article continuous body to be described later is shown, to explain the joint state of the mini-sheet piece 14. And FIG. 6 and FIG. 7 are explanation views where the use state of the interlabial pad 1 is shown.

Figure 5:
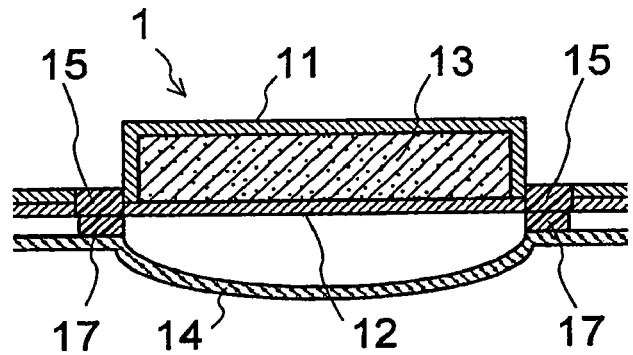
FIG. 5A is a schematic cross section view where a section in the lateral direction of the interlabial pad of FIG. 1 is shown.
FIG. 5B is a schematic cross section view where a section in the lateral direction of the interlabial pad of FIG. 1 is shown.
FIG. 5C is a schematic cross section view where a section in the lateral direction of the interlabial pad of FIG. 1 is shown.
FIG. 5D is a schematic cross section view where a section in the lateral direction of the interlabial pad of FIG. 1 is shown.
Figure 5:
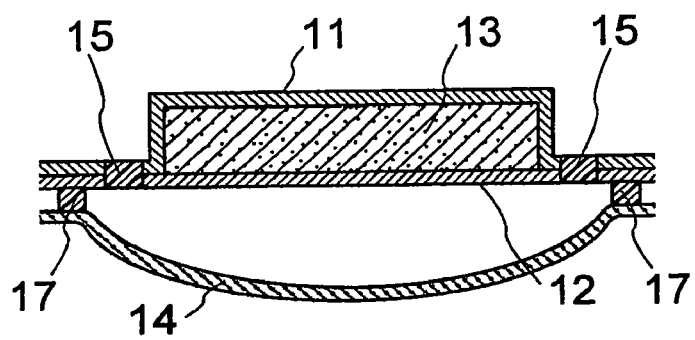
Figure 5:
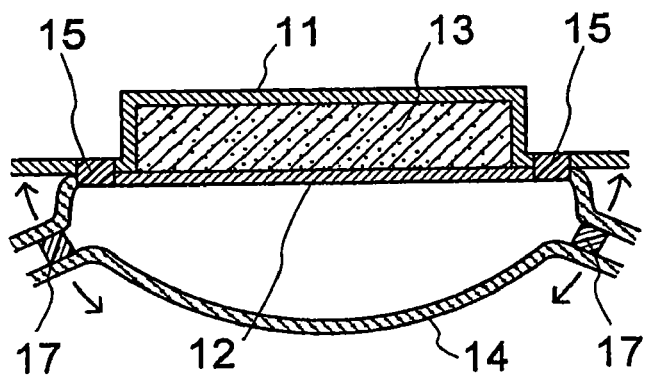
Figure 5:
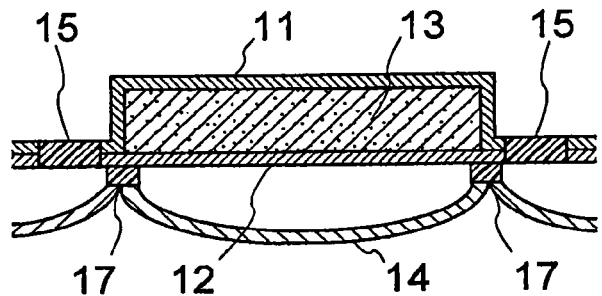

As shown in FIG. 5A, the portion of the joint part 15 becomes hard when the joint part 15 and the mini-sheet joint part 17 are joined at the position overlapping a laminating direction (vertical direction in FIG. 5) where the surface side sheet 11, the back side sheet 12, and the mini-sheet piece 14 are laminated, and the wearing feeling of the interlabial pad 1 will be deteriorated.

This can be evaded by joining the mini-sheet piece 14 by arranging the joint part 15 and the mini-sheet joint part 17 so as not to overlap in the direction of lamination, as shown in FIG. 5B. However, it is thought that there is also a possibility that the mini-sheet joint part 17 will move according to the wearer's motion, and stimulate the wearer because of the friction occurred between moving mini-sheet joint part 17 and the human body, as shown in FIG. 5C, when the concerned mini-sheet joint part 17 is located more outside than the portion of the joint part 15 as shown in FIG. 5B. Consequently, in case of execution, it is desirable to shift the position in the thickness direction of the joint part 15 and the mini-sheet joint part 17, to arrange the mini-sheet joint part 17 more inside than the portion of the joint part 15, as shown in FIG. 5D.

Figure 6:
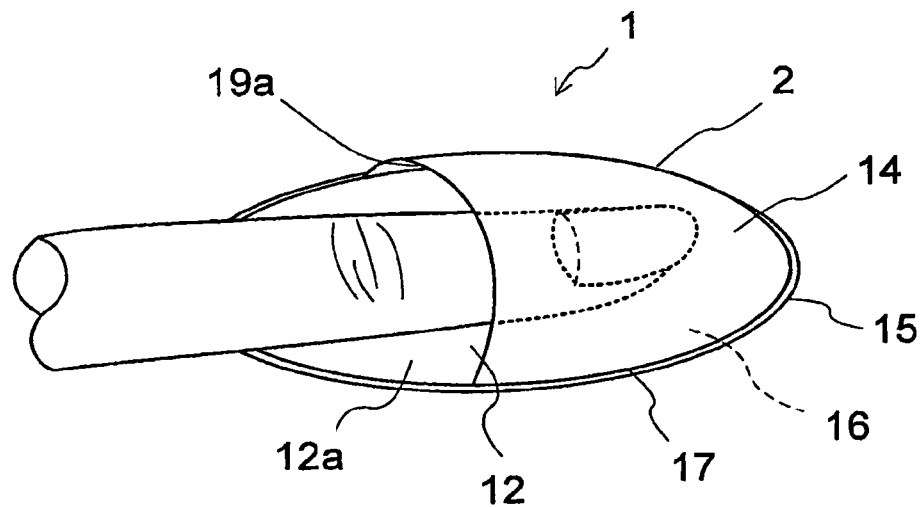
FIG. 6 is a view showing the state where a finger is inserted into a pocket for finger insertion provided on the interlabial pad of FIG. 1.
Figure 7:
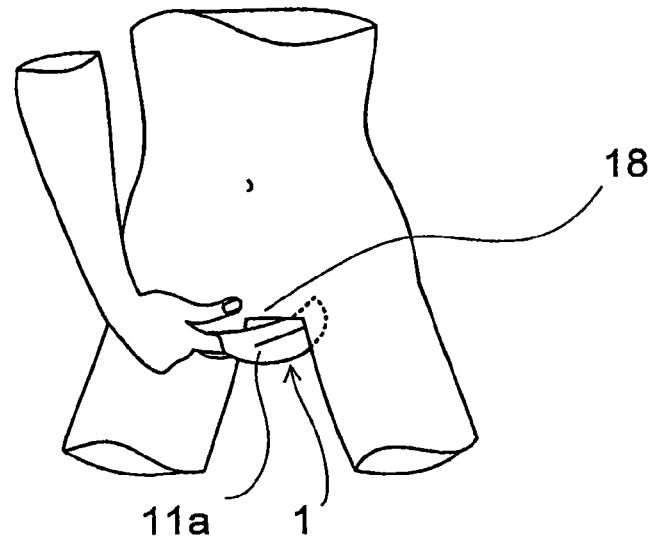
FIG. 7 is a view showing the state where the interlabial pad of one embodiment according to the present invention is to be fitted between labia.

The fingerprint face side of the first joint of a finger can be inserted in touch with the opposite body side face to body side face 12a of the back side sheet 12, as shown in FIG. 6, by inserting the tip of the finger into a pocket 16 formed between this back side sheet 12 and the mini-sheet piece 14.

Here, the part of the opposite body side face to body side face 12a which is not covered with the mini-sheet piece 14 and exposed outside acts as a finger insertion guide part when the finger to be inserted is inserted in the pocket 16, because the opposite body side face to body side face 12a is formed with a back side sheet 12 which is continuous through the part forming the pocket 16 and the part not forming the pocket 16. In other words, the wearer will be able to ready to use as shown in FIG. 6 by a simple operation like inserting a hand into a pocket, by allotting a finger to the opposite body side face to body side face 12a exposed outside acting as the finger insertion guide part, and sliding the finger toward the finger insertion opening 19a of the pocket 16 formed between the mini-sheet piece 14 and the opposite body side face to body side face 12a covered with the concerned mini-sheet piece 14.

And, the absorbent layer 2 which is formed integrally by joining the surface side sheet 11 and the back side sheet 12 at the joint part 15 on the surrounding edge of both sheets so as to seal the absorbent body 13, has such flexibility of the order that a tip of a finger can feel the uneven part of the labia where the surface side sheet 11 is applied, with the finger being inserted in the pocket 16 and the ball of the finger being in contact with the opposite body side face to body side face 12a of the back side sheet 12. In this point, it becomes easy to fix an interlabial pad at a proper position by hand feeling, compared with the one expected to be formed with a comparatively hard material, aiming to maintain a solid shape like the conventional Japanese Patent Publication No. 2001-509402. In other words, the body side face 11a of the surface side sheet 11 can be brought into contact with the labia 18, guided accurately in the labia 18 that are concave by feeling the uneven part of labia 18 by the sensitive ball of finger, when the interlabial pad 1 is induced to the labia 18 as shown in FIG. 7, in a state where the fingerprint side face of the first joint of a finger is brought into contact with the opposite body side face to body side face 12a of the back side sheet 12 and inserted, as shown in FIG. 6.

Moreover, when the interlabial pad 1 is detached from the labia 18, it is possible to detach it easily making neither the hand nor the finger dirty, because it is possible to detach it by inserting a finger into the pocket 16 by such a simple operation to insert a finger into the pocket like inserting a hand into a pocket, by allotting the finger to the opposite body side face to body side face 12a exposed outside acting as the finger insertion guide part, similarly to its fitting, and sliding the finger toward the finger insertion opening 19a of the pocket 16 formed between the mini-sheet piece 14 and the opposite body side face to body side face 12a covered with the concerned mini-sheet piece 14.

In a word, the body side face 11a of the surface side sheet 11 can be brought into contact with the labia 18, guided accurately in the labia 18 that are concave by feeling the uneven part of labia 18 by the sensitive ball of finger, when the interlabial pad 1 is induced to the labia 18 as shown in FIG. 7, in a state where the fingerprint side face of the first joint of a finger is inserted into the opposite body side face to body side face 12a of the back side sheet 12 being contacted it, as shown in FIG. 6.

It should be appreciated that the mini-sheet piece 14 can show that the finger insertion direction is the direction of the arrow 30, by affording a length in the range of 10% or more in the longitudinal direction for the absorbent layer 2, and being provided at a position biased in the longitudinal direction of the back side sheet 12. In this sense, the mini-sheet piece which has a "length of 10% or more of the absorbent layer 2" plays a role to hint the finger insertion direction, in the interlabial pad 1 according to the present invention.

Figure 8:
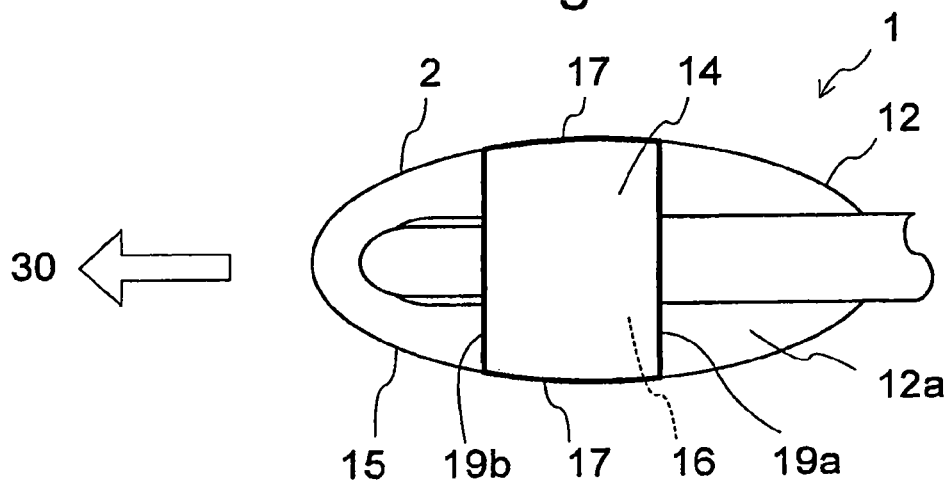
FIG. 8 is a view showing the state where a finger is inserted into the interlabial pad of one embodiment according to the present invention.
Figure 9:
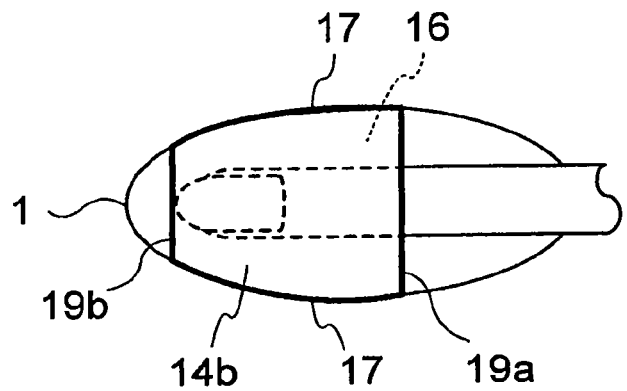
FIG. 9A is a plan view where the interlabial pad of one embodiment according to the present invention is shown.
FIG. 9B is a plan view where the interlabial pad of one embodiment according to the present invention is shown.
Figure 9:
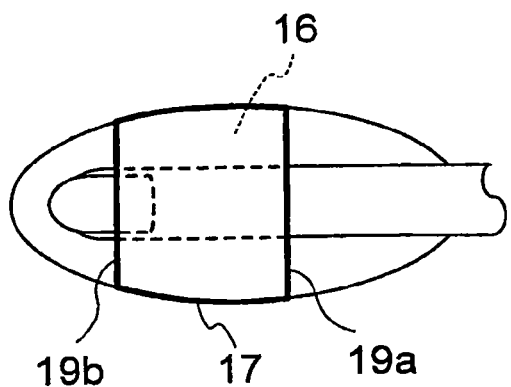

Moreover, the mini-sheet piece 14 and the back side sheet 12 are not joined in a finger insertion opening 19a which forms a first straight line part nor a second straight line part 19b located at the opposite position to the finger insertion opening 19a, in the embodiment shown in FIG. 8 and FIG. 9 B. However, the second straight line part 19b is joined to the opposite body side face to body side face 12a of the back side sheet 12 as in FIG. 9A. In this case, the tip of a finger will not be exposed, unlike the case shown in FIG. 9 B, because the wearer's tip of a finger is completely hidden by the second straight line part 19b, and it is hygienic. The shape of the line of the straight line part 19a and 19b is not restricted to straight, it can be wavy or curve and so on.

It should be appreciated that, in Japanese Patent Publication No. 6-506368, a urine incontinence prevention pad that has a bag shaped finger insertion hole provided on a face opposite to the body side is disclosed; however, as the finger insertion hole is described to be "in the collapsed state in the normal state, but expanded if a finger is inserted", there is drawbacks in the use state that the finger insertion hole is closed in the normal state, and the finger cannot be inserted in the insertion hole, if the finger is not directed to the direction which is right-angled with the urine incontinence prevention pad, or, an act of making efforts to insert a finger into a linear finger insertion opening in the collapsed state is required, and so on.

In a word, inconveniences that the finger insertion is difficult to perform with the hand feeling may be prospected, and it will be necessary to insert a finger aiming as the concerned insertion hole, compared with the one where a finger can be inserted into the pocket 16 by such a simple operation like inserting a hand into a pocket, by allotting the finger to the opposite body side face to body side face 12a exposed outside acting as the finger insertion guide part, and sliding the finger toward the finger insertion opening 19a of the pocket 16 formed between the mini-sheet piece 14 and the opposite body side face to body side face 12a covered with the concerned mini-sheet piece 14, as this embodiment.

Size of the Interlabial Pad

The length in the lateral direction of the interlabial pad 1 is preferably 10 to 60 mm and more preferably 30 to 50 mm. In this case, when it is longer than 60 mm, wearer's thigh and the surrounding edge part of the interlabial pad 1 come in contact, and friction is caused among them every time the wearer moves. And, the concerned interlabial pad 1 might drop out from labia, when such friction exceeds the power of the labia themselves maintaining the interlabial pad 1. On the other hand, when it is shorter than 10 mm, an area or volume enough to interpose the interlabial pad 1 between labia cannot be possessed, and the concerned interlabial pad 1 may drop out easier.

The length in the longitudinal direction of the interlabial pad between the labia is preferably 60 to 150 mm, and more desirably 80 to 120 mm. When it is longer than 150 mm, in this case, the contact area between the opposite body side face to body side face of the interlabial pad and the undergarment and so on is too large, and a friction force will be stronger than the retention force of the labia themselves maintaining the interlabial pad 1, and the interlabial pad 1 may drop out. On the other hand, when it is shorter than 60 mm, an area or volume is not enough to interpose the interlabial pad 1 between labia, and the concerned interlabial pad 1 may drop out easier.

The thickness of the interlabial pad is preferably 0.5 to 20 mm and more desirably 2 to 10 mm. The wearer feels uncomfortable when wearing it, if the thickness is 20 mm or more, because the interlabial pad is fitted between sensitive labia. On the other hand, if it is 0.5 mm or less, the capacity of the enclosed absorbent body tends to become insufficient for the absorption of menstrual blood, and the menstrual blood might begin to permeate from the interlabial pad.

A hydrophilic material that would not stimulate the skin is used for the water permeable sheet arranged on the body side of the interlabial pad. As such, materials which are made of any single or combination of nonwoven fabrics made by melt blowing, spun bonding, point bonding, through air, needle punching, wet-type spun lace, foam film, and so on can be enumerated.

Elements of the Interlabial Pad
Water Permeable Sheet

For the water permeable sheet of the interlabial pad facing the body, materials which are hydrophilic and non-irritant to the skin are used. Examples of these materials include materials which are made of any single or combination of nonwoven fabrics made by melt blowing, spun bonding, point bonding, through air, needle punching, wet-type spun lace, foam film, and so on. Examples of fibrous sheets include sheeted fabrics which are any single or mixture of fibers made of any single of rayon, acetate, cotton, pulp or synthetic resin, or fibers made by combining these fibers to form core and sheath structure.

Among the materials, considering the liquid mobility from the inner face of the labia and chemical stimulation by an activator, it is preferable a spun lace nonwoven fabric prepared in the following manner that the fiber in which the proportion of 5 to 30% of natural cotton and 70 to 95% of rayon or acetate are blended and is prepared to have 20 to 50 g/m$^2$, then the fibers are entangled to each other by water-flow interlacing treatment and then dried to prepare spun lace nonwoven fabric with the thickness of 0.3 to 1.0 mm. The fiber used for the above-described one is selected from natural cotton with the fiber length of 15 to 60 mm, rayon or acetate with the fiber length of 25 to 51 mm, and of 2.2 to 6.6 dtex.

Absorbent Body

As materials for the absorbent body, any single or combination of materials, such as pulp, chemical pulp, rayon, acetate, natural cotton, polymer absorbent, fibrous polymer absorbent and synthetic fiber, can be used. Materials for sheets may be used after processed into sheets or powder, not being limited by the application.

It is preferable for the absorbent body, although any material can be used as long as it is capable of absorbing and holding liquid (fluid), to be bulky, hard to be deformed, and less chemically stimulant. Specifically, a nonwoven fabric sheet can be used which is prepared in the following manner that the fiber is obtained by mixing and laminating in the proportion of 60 to 90% of rayon or acetate in the range of 1.1 to 4.4 dtex and 10 to 40% of fiber polymeric absorber, and then entangled and formed to be a sheet by needling, with a specific weight per unit area of 150 to 500 g/m$^2$ and the bulkiness of 2 to 5 mm.

When the absorbent above-described is enclosed inside the interlabial pad, it is possible to adjust the bulkiness by stacking or folding when necessary.

Water Impermeable Sheet

As the materials for the water impermeable sheets used for the interlabial pad, materials which can prevent the menstrual flow contained in the absorbent body from leaking out of the interlabial pad can be used. Using moisture-permeable materials will reduce the hot and muggy feeling, which will reduce the discomfort in use.

Examples of such materials include sheet films made of synthetic resins which are formed into membranes, breathing films made by drawing with inorganic fillers, paper, laminated materials made by combining nonwoven fabrics and films and porous waterproof sheets having 0.1 to 0.6 mm-diameter openings covering 10 to 30% of the total area with capillaries located to extend toward the absorbent.

Additionally, in considering flexibility so as not to degrade the feel in use, a film having a weight per unit area of 15 to 30 g/m$^2$ and mainly made of low density polyethylene (LDPE) resin which has a density of 0.900 to 0.925 g/cm$^3$ can be used as a preferred example.

Mini-Sheet Piece

For a mini-sheet piece, the same materials as for above-described water permeable sheets and water impermeable sheets can be used and it is preferable to use materials having at least breadthways extensibility or flexibility.

By using such materials for the mini-sheet piece, even if the wearer's finger is larger than the provided finger insert hole, the mini-sheet piece can stretch at least to the lateral direction corresponding to the wearer's finger size. This allows the wearer to use the interlabial pad effectively regardless of the wearer's finger size.

Examples of materials essentially having elasticity include styrene-ethylene-butadiene-styrene block copolymer (SEBS), styrene-butadiene-styrene block copolymer (SBS), styrene-isoprene-styrene block copolymer (SIS), synthetic rubber such as urethane rubber, films made from amorphous olefin resin having a density of 0.88 to 0.900 g/cm$^3$, opening foam film and net. Woven fabrics or fabrics in which spun filaments made from synthetic rubber are interwoven can also be used. In addition, a spun bond nonwoven fabric, a melt blown nonwoven fabric and expanded foam sheet which mainly made from synthetic rubber can also be used.

In considering a soft feel in use, a preferred example is a porous foam film opening foam film made from SBS, adjusted to be a thickness of 15 to 40 micrometer and constructed to have pores of 0.28 to 1.77 mm$^2$, and a porosity of 40 to 70%.

Examples of nonwoven fabric include materials which mainly made of heat shrinkable compound synthetic fibers having a high-melting core part and a low-melting sheath part, such as polyethylene (PE)/polypropylene (PP), PE/polyethylene terephthalate (PET), PP/PP; including a spun lace nonwoven fabric whose fibers are entangled by water streams, shrink-type nonwoven fabric whose fibers are shrunk by reheating air processing and so-called extensible spun bond, which is a sheet made from continuous long fiber by heat sealing and forced tendering in the longitudinal direction.

More specifically, a shrink-type nonwoven fabric which mainly made of heat shrinkable compound synthetic fibers having a fineness of 2.2 to 6.6 dtex, a length of 38 to 51 mm, high-melting core part and low-melting sheath part, such as PE/PP, PE/PET, PP/PP and adjusted to have a weight per unit area of 20 to 60 g/m$^2$ is a suitable material having a suitable softness and drape. Laminated materials made of the materials described above can also be used.

When using non-extensible materials which are processed to have extensibility, the examples of the materials include any single or combination of nonwoven fabrics which mainly made of heat shrinkable compound synthetic fibers having high-melting core part and low-melting sheath part, such as PE/PP, PE/PET, PP/PP, including a bulky through air nonwoven fabric which is processed by hot air, a spun lace nonwoven fabric whose fibers are entangled by water streams, spun bond nonwoven fabric sheets made by layering continuous fiber, a needle punch nonwoven fabric whose fibers are entangled with needles and a SMS nonwoven fabric formed into sheets by multi-layering spun bond and melt blown fabrics, and opening foam film and films mainly made of PE resin.

It is also possible to provide the above-described materials with extensibility using corrugate processing, in which the material is placed between male-female molds and embossed by heat, temperature and pressure. More specifically, the examples include a through air nonwoven fabric which mainly made of compound synthetic fibers adjusted to have a fineness of 2.2 to 4.4 dtex and a weight per unit area of 20 to 60 g/m$^2$ and applied corrugate processing to have breadthways extensibility. Preferably, the male-female molds of the corrugate processing is arranged to achieve an extensibility at least 10%, and more preferably, to have an extensibility of 20 to 50%, yet more preferably, the processed material is extended by 30% with a load of 0.01 to 0.05 N/25 mm (Test condition: using TENSILON tensile testing apparatus, rate: 100 mm/min., chuck interval: 100 mm).

For providing the materials with extensibility, methods such as making incisions or perforating can be used.

Joint Part

Any means can be selected as the joining means to join the surface side sheet and the absorbent body, the absorbent body and the back side sheet, the surface side sheet and the back side sheet, and the back side sheet and the mini-sheet piece. For instance, the joining means include joining by adhesive, joining by heat emboss and so on. For the adhesive, a pressure sensitive adhesive made mainly of a synthetic rubber such as SEBS, SBS, SIS and the like, the heat sensitive adhesive made mainly of a synthetic rubber such as ethylene-vinyl acetate copolymer (EVA) and the like, the adhesive made mainly of a water soluble, plastic polyvinyl alcohol (PVA) resin, a water sensitive gel made mainly of a starch glue or acrylic acid and the plasticizer or a water, a non water sensitive gel made mainly of a silicone, a crosslinking agent, and the plasticizer, are eligible.

Sticky Part

A sticky part may be formed in the interlabial pad, by applying a sticky material on the surface side sheet. The interlabial pad having the sticky part on the surface side sheet, where the sticky material was spread, is fixed to the body by the sticky material more certainly, and maintained in the labia.

As the sticky materials which can be used, a gel sticky material containing a water-soluble polymer, a crosslinking agent, a plasticizer, and water can be mentioned. To be more concrete, as examples of the water-soluble polymers, gelatin, sodium polyacrylate, PVA, carboxyl-methyl-cellulose, etc. can be mentioned; as examples of the crosslinking agents, water-soluble metal salt such as calcium chloride, and magnesium sulfate generally used; and as examples of the plasticizers, glycerine, wax, paraffin, etc. can be mentioned.

In addition to the above, a pressure-sensible hot melt type sticky material can also be used as a sticky material for forming the sticky part. The pressure-sensible hot melt sticky material consists essentially of a synthetic rubber resin such as SIS, SBS, SEBS, and styrene-ethylene-propylene-styrene block copolymer (SEPS), and can be obtained by melt-blending therein a tackifier such as turpentine resin and rosin resin, and a plasticizer such as wax. Further, silicone resin sticky materials can be used. As the silicone resin sticky material, a mixture composed by blending of crosslinking agents which essentially consist of silicone resin or fluorocarbon polymer and is metal salt of platinum, molybdenum, antimony, etc., and a polymerizer such as ester wax, glycerine, machine oil, etc.

Thus, there are many kinds of sticky materials for forming the sticky part, however, considering the stability of application, a pressure sensitive hot melt sticky material is preferred for the use. As the pressure sensitive hot melt adhesive with high application stability, a melt-blended mixture of 15 to 25 percent by mass SEBS, 15 to 35 percent by mass plasticizer, and 40 to 70 percent by mass tackifier can be mentioned. An oxidation inhibitor, a fluorescence inhibitor, etc. may be added to this pressure sensitive hot melt sticky material within a range of 0.1 to 1.0 percent by mass.

Furthermore preferably the sticky part is coated by a sheet comprised of a tissue paper used for a separate paper on which silicone resin is coated and by a sheet comprised of a plastic film on which silicone resin is coated. Thereby damage and a separation of the sticky part during the interlabial pads being stored can be prevented.

Structure of the Interlabial Pad Provided to be Biodegradable, Water Dispersible and Water Soluble Preferably the interlabial pad of the present invention is comprised of a material of biodegradable and/or a material of water dispersible and/or a material of water-soluble. After the pad comprised of these materials is used, it can be disposed into a toilet to flush, thereby the destruction of the pad can be easily and sanitarily achieved and the garbage in a toilet can be decreased.

In this Specification, "biodegradable" means that a substance is decomposed to a gas such as carbon dioxide or methane and so on and water or biomass under anaerobic or aerobic condition according to the natural process under the existence of bacteria represented by actinomycetes and other microbes, and also means that the biodegradability (biodegradable rate or biodegradable degree) of the substance equals to a material naturally generated such as fallen leaves or a synthetic polymer generally recognized having the same biodegradability under the same environment. "Water dispersible" has the same meaning as water break down. It means a characteristic in which, while having no influence when used in a limited amount of moisture (menstrual blood), in a large amount of water or water current, the fabric is easily dispersed into small pieces at least to a degree where an ordinal toilet plumbing is not clogged. "Water soluble" is a characteristic in which, while having no influence when used in a limited amount of moisture (menstrual blood), the fabric is soluble in a large amount of water or water current.

Water Permeable Sheet

As the materials for water permeable sheets, along with a spun lace nonwoven fabric, wet-process spun lacing nonwoven fabric selected from the nonwoven fabrics within a range of fiber length of 1 to 15 mm can be used. In addition to the above-described materials, biodegradable resins which are gained by hydrolysis process of such as polylactic acid, polybutylene succinate can also be used. For example, a melt blown nonwoven fabric which is made from polylactic acid and adjusted to have a weight per unit area of 20 to 60 g/m$^2$ or a spun bond nonwoven fabric adjusted to have a weight per unit area of 15 to 30 g/m$^2$ and a fineness of 1.1 to 3.3 dtex can be used. For each nonwoven fabric material, aperturing is optional.

As the other materials, the tow of synthetic fiber or of continuous fiber of the laminated body may be used by adjusting to a range of weight per unit area of 50 to 300 g/m² to ravel fiber each other.

Absorbent Body

As the materials for absorbent body, nonwoven fabric sheets made by needling can be used. Considering the biodegradability of polymer absorbent body, it is preferable to use carboxymethyl cellulose fibers.

Water Impermeable Sheet

As materials for water impermeable sheet, polyvinyl alcohol (PVA) films, film sheets made by applying water-repellent processing on one side, both sides or some parts of PVA films using silicone and so on, PVA films mixed with silicone, starch films, laminated paper consisting of films made of resins which are gained by hydrolysis process of such as polylactic acid and polybutylene succinate, and tissue and so on. The materials may be colored by mixing inorganic pigments within a range of 0.1 to 5% as required.

When maintaining leakage prevention in humid conditions and avoiding an excessive load on purification tank are taken into consideration, a preferred material is laminated paper made by laminating a film made from polylactic acid to tissue having a thickness of 10 to 20 μm and a weight per unit area of 15 to 20 g/m², with a bonded area of 5 to 40% of laminated area.

Mini-Sheet Piece

As materials for the mini sheet piece, films, a spun bond nonwoven fabric and a melt brown nonwoven fabric made from biodegradable resins, such as polylactic acid, polybutylene succinate; films and nonwoven fabrics made from water-soluble materials such as PVA and CMC; and water dispersible tissue and a spun lace nonwoven fabric mainly consisting of cellulose fibers, regenerated cellulose and others can be used.

It is preferable to use sheets of a spun bond nonwoven fabric or a melt blown nonwoven fabric, which mainly consist of biodegradable materials, are adjusted to have a fineness of 0.1 to 3.3 dtex and a weight per unit area of 15 to 40 g/m² and are subjected to the mechanical corrugate processing.

Attachment or detachment of the interlabial pad to or from the body can be made by the finger insertion opening by an easy operation decreasing a fear for the dirt of the hands by allotting a finger to the finger insertion guide part, by a novel interlabial pad as mentioned bellow. In other words, an "interlabial pad comprising an absorbent layer including a water permeable surface side sheet to be brought into contact with the body side, a back side sheet arranged in opposition to the surface side sheet, and an absorbent body for absorbing body fluid between the water permeable surface side sheet and the back side sheet, wherein the absorbent layer has the size, the weight, and the flexibility that allows to obtain a retention force by arranging a part or the whole of the absorbent layer between labia of the body, and moreover, a part of the opposite body side face to body side face of the absorbent layer is provided with a pocket with a finger insertion opening as fixing means for allowing to attach/detach the concerned absorbent layer to and from the body, the area of the opposite body side face to body side face of the absorbent layer not covered with the pocket is exposed to the exterior, and the opposite body side face to body side face of this exposed absorbent layer guides a finger to the concerned finger insertion opening when the finger is inserted into the finger insertion opening," can be provided.

The interlabial pad mentioned above can be produced by the following producing steps.

Hereinafter, one embodiment of the present invention shall be described referring to the drawings.

The Process of First Production Method

The first method for producing an interlabial pad of an embodiment of the present invention shall be described referring to FIG. 10A and FIG. 10B. FIG. 10A shows an apparatus for producing an interlabial pad which is an embodiment of the present invention, comprising a main part assembly unit 301, a mini-sheet assembly unit 302, a concurrent regular joining unit 303, a folding unit 304 and a round cut unit 305. The main part assembly unit 301 has a mechanism of supplying a surface side sheet continuous member for supplying the surface side sheet continuous member 110, a mechanism of supplying a back side sheet continuous member for supplying the back side sheet continuous member 120, a mechanism of supplying an absorbent body for supplying the absorbent body and a mechanism of assembling a main part continuous body. In FIG. 10A, the mechanism of supplying a surface side sheet continuous member includes a first rolling roller 810 rolling a raw fabric roll of surface side sheet 110a and a first drawing roller 811 for drawing out the raw fabric roll of surface side sheet 110a and feeding the raw fabric roll of surface side sheet to the mechanism of assembling a main part continuous body. The mechanism of supplying a back side sheet continuous member includes a second rolling roller 820 rolling the raw fabric roll of back side sheet 120a and a second drawing roller 821 for drawing out the raw fabric roll of back side sheet 120a and feeding the raw fabric roll of back side sheet it to the mechanism of assembling a main part continuous body. The mechanism of supplying an absorbent body includes a fourth rolling roller 830 for rolling the raw fabric roll of absorbent body 130a. The mechanism of assembling a main part continuous body has a plurality of assembling rollers 113, 123, 133. The mechanism of supplying an absorbent body is positioned between the mechanism of supplying a surface side sheet continuous member and the mechanism of supplying a back side sheet continuous member, arranges the absorbent body between the surface side sheet continuous member 110 which is fed from the mechanism of supplying a surface side sheet continuous member, and the back side sheet continuous member 120, which is fed from the mechanism of supplying a back side sheet continuous member. A first meander correcting mechanism 111 and a second meander correcting mechanism 121 may be provided as necessary on the mechanism of supplying a surface side sheet continuous member and the mechanism of supplying a back side sheet continuous member, respectively.

It should be appreciated that, in this embodiment, the mechanism of assembling a main part continuous body has a first hot melt type adhesive spreading mechanism 112 for spreading the hot melt type adhesive to the surface side sheet continuous member 110 and a second hot melt type adhesive spreading mechanism 122 for spreading the hot melt type adhesive to the back side sheet continuous member 120 in order to temporary join at least the surface side sheet continuous member 110 and the back side sheet continuous member 120 by the hot melt type adhesive. The main part assembly unit 301 may have a cutting mechanism, in order to arrange the absorbent body between the surface side sheet continuous member 110 and the back side sheet continuous member 120, after the absorbent body continuous member is cut into each absorbent body.

The mini-sheet assembly unit 302 has a mechanism of supplying a mini-sheet piece for supplying a mini-sheet piece and a mechanism of attaching a mini-sheet piece for forming the sanitary absorbent article continuous body 220 by arranging and joining the mini-sheet piece on the opposite body side face to the body side face of the back side sheet continuous member 120 of the main part continuous body 200. The mechanism of supplying a mini-sheet piece includes a third rolling roller 840 for rolling the raw fabric roller of mini-sheet 140a and a third drawing roller 841 for drawing out the raw fabric roller of mini-sheet 140a and feeding the raw fabric roll of mini-sheet 140a to a mechanism of attaching a mini-sheet. The mechanism of attaching a mini-sheet includes a first feeding roller 850 for feeding the main part continuous body 200, a first feeding belt 851 and a suction roller 143 for arranging the mini-sheet piece on the side to the body side of the back side sheet continuous member 120 of the main part continuous body 200.

The concurrent regular joining unit 303 includes a concurrent regular joining mechanism 60 for regularly joining the joint part and the mini-sheet part, and the concurrent regular joining mechanism 60 includes a first concurrent regular joining upper roller 61 and a second concurrent regular joining lower roller 62 for compressing a laminated body of the main part continuous body 200 and the mini-sheet piece fed from the mini-sheet assembly unit 302.

The folding unit 304 includes a folding mechanism, and the folding mechanism includes a plurality of second feeding rollers 860.

The round cut unit 305 includes a cutting mechanism 90 and the cutting mechanism 90 includes a cutter roller 91 having a cutter blade.

The first method of one embodiment of be present invention for producing interlabial pads using the apparatus mentioned above and comprises a) a main part assembly step that forms a main part continuous body 200 by arranging a surface side sheet continuous member 110 comprising continuous materials, which form surface side sheets to be positioned on the body side when worn and a back side sheet continuous member 120 comprising continuous materials which form back side sheets to be positioned on the opposite side to the body side, so as to enclose an absorbent body 13 b) a mini-sheet assembly step that forms a sanitary absorbent article continuous body by spreading temporary joining means such as adhesives to a part or the whole of one of the surface of a mini-sheet piece continuous member 140 comprising continuous materials from which mini-sheet pieces are made, positioned in contact with back side sheet continuous member 120, separating the mini-sheet piece continuous member into two or more mini-sheet pieces by cutting to a prescribed length on a suction roller 143, and joining the concerned mini-sheet piece to a face that becomes the opposite body side face to body side face of the back side sheet continuous member 120 temporally from the suction roller 143;

c) a concurrent regular joining step that regularly joins the absorbent body, the surface side sheet continuous member 110, the back side sheet continuous member 120 and the mini-sheet piece continuous member to one body, or the surface side sheet continuous member 110, the back side sheet continuous member 120, and the mini-sheet piece continuous member except the absorbent body mutually at a joint part on the surrounding edge of the absorbent body;

d) a folding step that folds the sanitary absorbent article continuous body 220 at a center crease provided along a direction where the sanitary absorbent article continuous body 220 is continuous; and e) a round cut step that forms the outer contour of individual interlabial pads by cutting off an unnecessary part of the folded sanitary absorbent article continuous body 220 with a prescribed width provided from the absorbent body.

Hereafter, the producing method of the first embodiment shall be described concretely.

Main Part Assembly Step

First of all, the supply of raw material shall be described. The surface side sheet continuous member 110 is drawn out from a raw fabric roll 110a of surface sheet continuous member through a first drawing roller 811, passed through a first meander correcting mechanism 111, and sent to a first hot melt type adhesive spreading mechanism 112. A joint in the side of the surface side sheet part is provided in a portion where the surface side sheet and the back side sheet are joined on the surface side sheet continuous member 110. Then, the surface side sheet continuous member 110 is sent to pass over the assembling roller 113 after the first hot melt type adhesive spreading mechanism 112 has continuously supplied the hot melt type adhesive to the surface side sheet side joint part of the surface side sheet continuous member 110.

On the other hand, the back side sheet continuous member 120 is drawn out from a raw fabric roll 120a of back sheet continuous member through a second drawing roller 821, passed through a second meander correcting mechanism 121, and sent to a second hot melt type adhesive spreading mechanism 122. A joint part in the side of the back side sheet is provided in a portion where the surface side sheet and the back side sheet are joined on the back side sheet continuous member 120. Then, the back side sheet continuous member 120 is sent to pass under the assembling roller 123 after the second hot melt type adhesive spreading mechanism 122 has continuously supplied the hot melt type adhesive to the back side sheet side joint part of the back side sheet continuous member 120.

Further, a continuous absorbent body formed with absorbent bodies continuously is drawn out from a raw fabric roll of absorbent body 130a, and cut into an individual absorbent body. Then, it is sent between assembling rollers 113 and 123, and arranged between the surface side sheet continuous member 110 and the back side sheet continuous member 120 to form the main part continuous body 200.

Here, the raw fabric roll 110a of surface side sheet continuous member is a material of the surface sheet of a sanitary absorbent article that becomes a product, and is a roll that wound up a continuous body from which the surface side sheet used for a plurality of sanitary absorbent articles can be cut out by cutting it at a substantially right-angle or a prescribed angle to the continuous direction. Similarly, the raw fabric roll 120a of back side sheet continuous member is a material of the back side sheet of a sanitary absorbent article that becomes a product, and is a roll that wound up a continuous body from which the back side sheet used for a plurality of sanitary absorbent articles can be cut out by cutting it at a substantially right-angle or a prescribed angle to the continuous direction. These raw fabric rolls 110a and 120a are arranged on the opposite sides in the vertical direction in respect to the producing line. In a word, the raw fabric roll 110a of surface side sheet and the raw fabric roll 120a of back side sheet are arranged opposite to each other in the vertical direction, and a mechanism of assembling a main part continuous body which arranges absorbent bodies between both side sheet continuous members is arranged between the raw fabric roll 110a of surface side sheet and the raw fabric roll 120a of back side sheet. In this case, the raw fabric roll 110a of the surface side sheet continuous member 110 may be arranged on the upper side or the lower side of the mechanism of assembling a main part continuous body. Similarly, the raw fabric roll 120a of the back side sheet also may be arranged either on the upper side or the lower side of the mechanism of assembling a main part continuous body as long as positioned opposite to direction of the surface side sheet continuous member. By making such arrangement, open space of the mechanism of assembling a main part continuous body can be used effectively and the apparatus for producing a sanitary absorbent article can be made compact, by arranging like this.

Thus, at the main part assembly step, the hot melt type adhesive is spread to each of the surface side sheet continuous member 110 and the back side sheet continuous member 120, then the surface side sheet continuous member 110 spread with the adhesive and the back side sheet continuous member 120 spread with the adhesive are arranged to sandwich the absorbent body therebetween and joined temporary in the main part assembly unit 301.

It may be appreciated that, at the main part assembly step, the back side sheet continuous member 120 and the absorbent body can be joined by spreading beforehand the hot melt type adhesive on a mutual contact face of the back side sheet continuous member 120 and the absorbent body. Similarly, the surface side sheet continuous member 110 and the absorbent body can be joined by spreading beforehand the hot melt type adhesive on a mutual contact face of the surface side sheet continuous member 110 and the absorbent body.

The hot melt type adhesive used in the main part assembly step in this embodiment is a temporary joining mean to fix the surface side sheet continuous member 110 and the back side sheet continuous member 120 at least temporarily with the absorbent body arranged between both sheet continuous members. Therefore, the hot melt type adhesive may be able to temporarily join the surface side sheet continuous member 110 and the back side sheet continuous member 120 by spreading at least a portion of the surface side sheet side joint part or the back side sheet side joint part, and the hot melt type adhesive may not need applied on either of the surface side sheet continuous member 110 or the back side sheet continuous member 120, and other adhesives of weaker adhesive power may also be used.

The hot melt type adhesive mentioned above is the one generally used as so-called hot melt applicator. Concretely, the hot melt type adhesive is melted by heating it in a not shown melting tank, sent forcefully to a supply hose with various pumps such as gear pump, plunger pump, or the like and the hot melt type adhesive sent in the manifold is discharged under pressure from a nozzle of a prescribed shape. The spreading pattern of this hot melt type adhesive can arbitrarily have shapes of the line, plane, spiral, omega in the upper case character, mist, reticulation, and so on, and a pressure sensitive hot melt type adhesive heated in the range of 120 degree Celsius to 180 degree Celsius is applied in the range of 1 to 10 g/m$^2$ by a specific weight per unit.

Moreover, in a preferable embodiment, it is desirable for the absorbent body not to be pinched in the joint part where the surface side sheet and the back side sheet are joined. For this purpose, for instance, only the surface side sheet continuous member 110 and the back side sheet continuous member 120 are temporarily joined in a part, and thereafter, the absorbent body is arranged to confine it in a portion enclosed like a bag by the joint part which is temporarily joined in a part. Concerning this, in case where the absorbent body is pinched in the joint part and joined, the concerned joint part turns up to become hard; however, in this embodiment, the concerned joint part is prevented from becoming hard and the wearing feeling becomes more comfortable, by avoiding the absorbent body being pinched in the joint part where the junction takes place, as mentioned above.

The size of the absorbent body may be equal to the surface side sheet and the back side sheet of the individual interlabial pad cut off from the sanitary absorbent article continuous body 220, and it may also be a size that is reduced so that an interval in the range of 2 to 10 mm from the outermost contour of the surface side sheet and the back side sheet may be provided, for preventing the absorbent body from being pinched in the joint part.

Mini-Sheet Assembly Step

Subsequently, the mini-sheet assembly step that attaches the mini-sheet piece shall be described.

In the mini-sheet assembly step, a mini-sheet piece continuous member 140 is drawn out from a raw fabric roll 140*a* rolled onto third roller 840, through a third drawing roller 841, passed through a third meander correcting mechanism 141 to send to a third hot melt type adhesive spreading mechanism 142, and a hot-melt adhesive is spread on a mini-sheet joint part in the side of the mini-sheet provided to join it to the back side sheet. The mini-sheet piece continuous member 140 is maintained on a suction roller 143 by applying a suction pressure by suction from the inside on the concerned suction roller 143 provided with two or more holes, and cut as it is into a prescribed length by a cutter roller having a cutting blade, and an individual mini-sheet piece is formed.

The mini-sheet piece cut into the prescribed length is arranged on the side of the back side sheet continuous member 120, and joined temporarily to the back side sheet continuous member 120 with the hot melt type adhesive spread beforehand. In this case, in order to prevent the wrinkle in the finished product, the speed at which the back side sheet continuous member 120 is fed is set equal to the speed at which the cut mini-sheet pieces are dropped. As a result, the finger insertion opening to insert a finger is formed between the back side sheet and the mini-sheet piece.

The hot melt type adhesive used for the mini-sheet assembly step in this embodiment is a temporary joining means to fix the back side sheet continuous member 120 and the mini-sheet piece at least temporarily. And, though the hot melt type adhesive is spread on the mini-sheet piece in this embodiment, it may be spread on the back side sheet side mini-sheet joint part provided on the side of back side sheet continuous member 120. That is, the hot melt type adhesive may be spread at least a portion of the mini-sheet joint part in the mind-piece or the mini-sheet joint part in the back side sheet, and other adhesives of weak adhesive power may also be used.

As for the hot melt type adhesive, pressure-sensitive hot melt type adhesives are used, a spreading pattern having shapes of the stripe, line, omega in the upper case character, and so on is desirable to stabilize the width of the finger insertion opening, and the one heated it in the range of 140 to 180 degree Celsius, and adjusted in the range of 5 to 100 g/m$^2$ by weight per unit is spread right and left respectively, leaving an interval for the formation of the finger insertion opening.

Concurrent Regular Joining Step

Subsequently, the concurrent regular joining step that joins regularly absorbent body, surface side sheet continuous member 110 and the back side sheet continuous member 120 regularly, at the same time as regularly joining the back side sheet continuous member 120 and the mini-sheet piece shall be described.

The absorbent body is supplied to arrange it between the surface side sheet continuous member 110 and the back side continuous sheet continuous member 120. And the absorbent body is supplied by matching the timing of the supply of the surface side sheet continuous member 110 and the back side sheet continuous member 120. A laminated body arranging the mini-sheet piece on the back side continuous sheet continuous member 120 of the main part continuous body 200 is passed between a first concurrent regular joining roller 61 and a second concurrent regular joining roller 62 of a concurrent joining mechanism 60. The joint part and mini-sheet joint part are formed, by joining the surface side sheet continuous member 110 and the back side sheet continuous member 120 and, at the same time, joining the back side sheet continuous member 120 and the mini-sheet piece by pressing from the upper side and the lower side with a pressurizing mechanism provided on the first concurrent regular joining roller 61 and the second concurrent regular joining roller 62. Thereby the surface side sheet continuous member 110 and the back side sheet continuous member 120 are joined mutually, and the mini-sheet piece is joined to the back side sheet continuous member 120, and the sanitary absorbent article continuous body 220 having the mini-sheet piece joined on the back side sheet continuous member is formed.

The first concurrent regular joining roller 61 has a smooth surface shape, while the second concurrent regular joining roller 62 is provided with an emboss pattern arranging emboss parts in 3 rows with an angle of 45°, emboss parts being adjacent by 0.7 mm² for each corner, and leaving an interval of 1 mm between the adjacent emboss parts. And, the first concurrent regular joining roller 61 has heat in the range of 70 degree Celsius to 120 degree Celsius and the second concurrent regular joining roller 62 has heat in the range of 90 degree Celsius to 140 degree Celsius respectively, and they are adjusted to have a line pressure of from 300000 to 900000 N/m, to perform a regular joining by heat seal.

Folding Step

Figure 10:
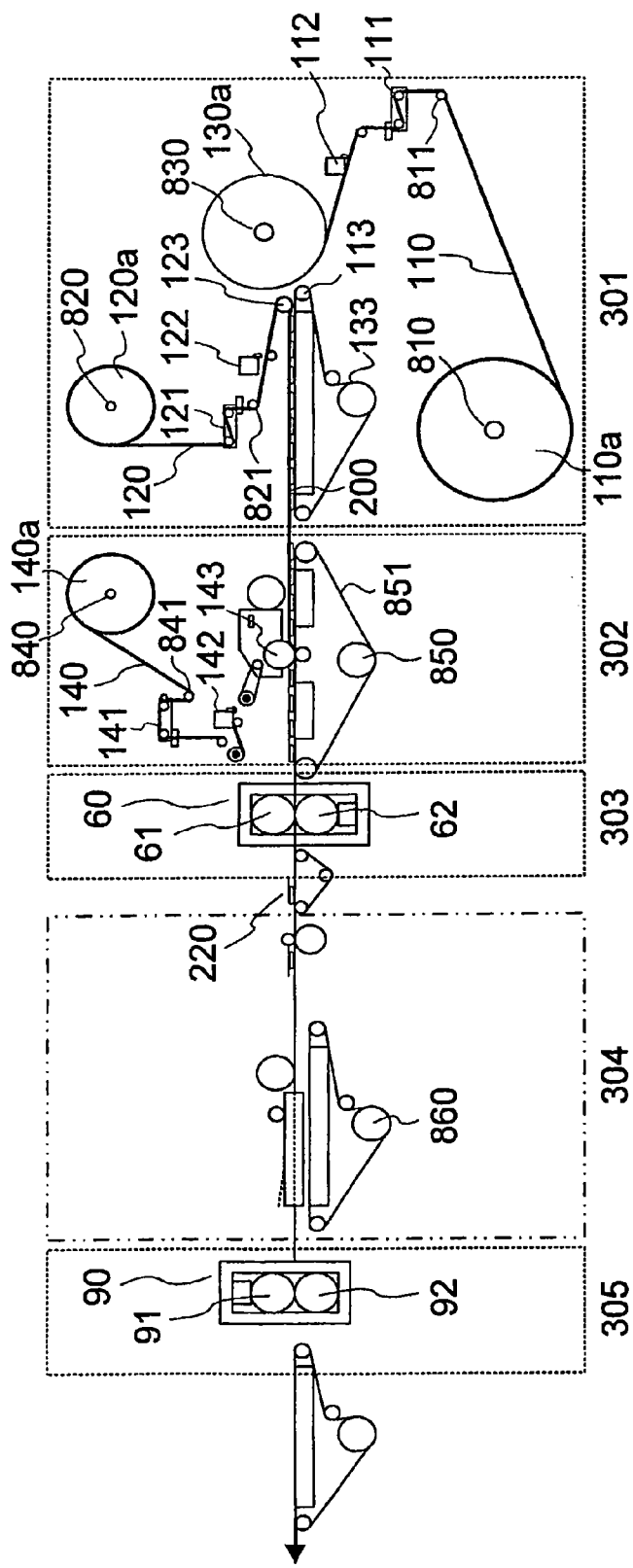
FIG. 10A is a side view of an apparatus for producing interlabial pad according to one embodiment of the present invention.
FIG. 10B is a schematic view that shows a folding unit, in the apparatus for producing interlabial pad of FIG. 10.
Figure 10:
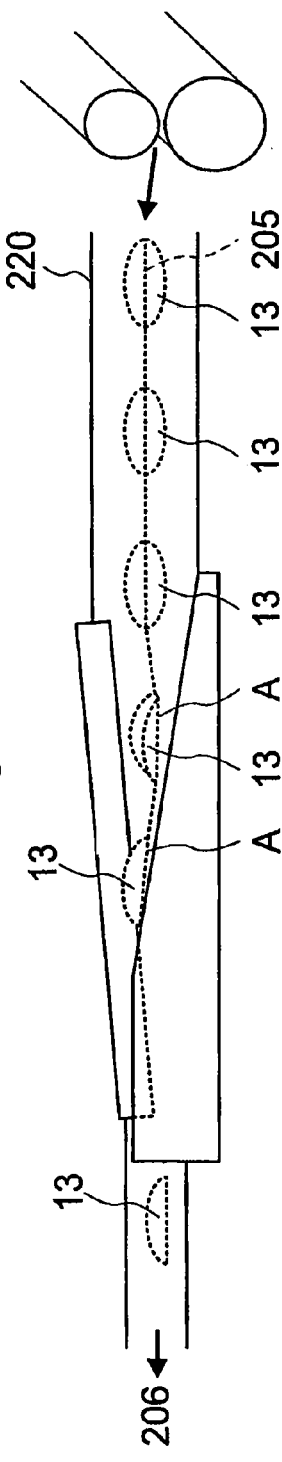

A sanitary absorbent article continuous body 220 is folded in the folding step so that the back side sheet continuous member 120 may become inside, along a center crease 205 provided for the direction (arrow 206 of FIG. 10 B) where the sanitary absorbent article continuous body 220 is continuous as shown in FIG. 10 B. The sanitary absorbent article continuous body 220 may be folded so that the surface side sheet continuous member 110 may become inside. The sanitary absorbent article continuous body 220 is cut off in the surrounding of the joint part as later described round cut step, after being folded along the center crease 205, and an individual sanitary absorbent article is produced.

Thus, it is possible to cut accurately, by cutting the sanitary absorbent article continuous body while it is folded in two, regardless of the presence of the enclosed absorbent body. The folding step can be omitted.

Round Cut Step

At the round cut step, the sanitary absorbent article continuous body 220 is sent to a cutting mechanism 90. The cutting mechanism 90 round cuts unnecessary parts of the structure of the interlabial pad as the finished product by cutting off the sanitary absorbent article continuous body 220 at the outer edge of joining part, by making the second concurrent regular joining roller 92 a receiving roller having a smooth surface and by applying pressure to the first concurrent regular joining roller 91 which is a cutter roller having a cutter blade. The sanitary absorbent article continuous body 220 is separated to the interlabial pad which corresponds to each unit of one product where a smooth and rounded outer contour is formed, by passing this cutting mechanism 90.

The completed individual interlabial pad is shipped, after the steps of wrapping, packing, and so on.

In order to further improve the stability during the round cutting, it is also desirable to have a folding habit step that forms a folding habit by means of a compression line, by folding the sanitary absorbent article continuous body 220 or the main part continuous body 200 along the center crease 205 before the round cut step. When the folded sanitary absorbent article continuous body 220 is cut off, a cut shape having an even right and left configuration having this step.

For instance, the compression line can be formed by emboss process using the so-called emboss roller or pattern roller and so on which is adjusted to have a line pressure of 300000 to 900000 N/m along the center crease 205 of the fed sanitary absorbent article continuous body 220, constitutes by forming a disk installed linearly and continuously, in respect to the production line flow direction, by heating a roller having a protrusion with a width of 0.5 to 3 mm and a flat roller to a range of the ambient temperature to 150 degree Celsius.

Figure 11:
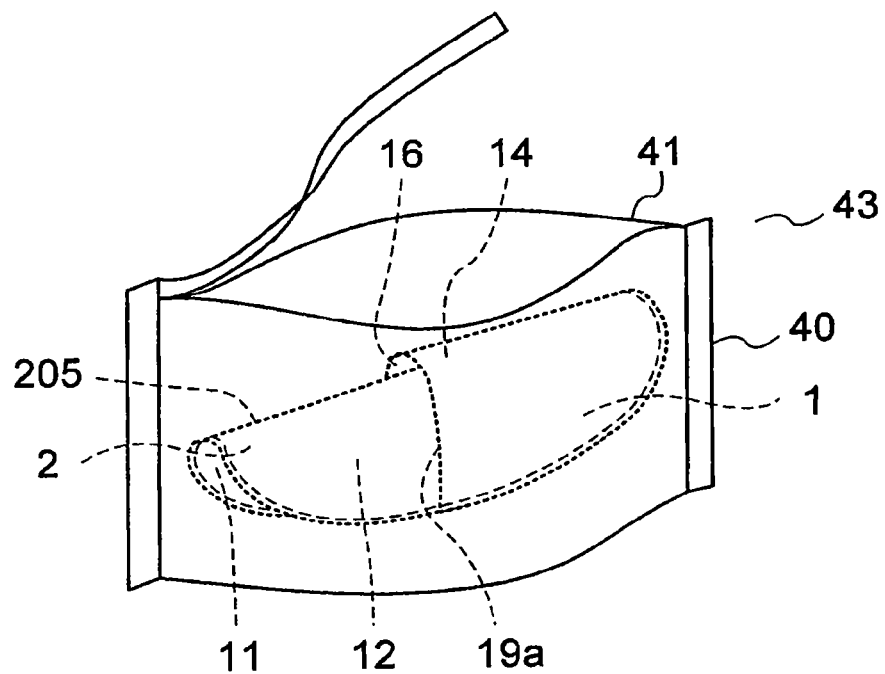
FIG. 11 shows the open state of an individual wrapping body where the interlabial pad according to one embodiment of the present invention is enclosed by folding the surface side sheet inside.
Figure 12:
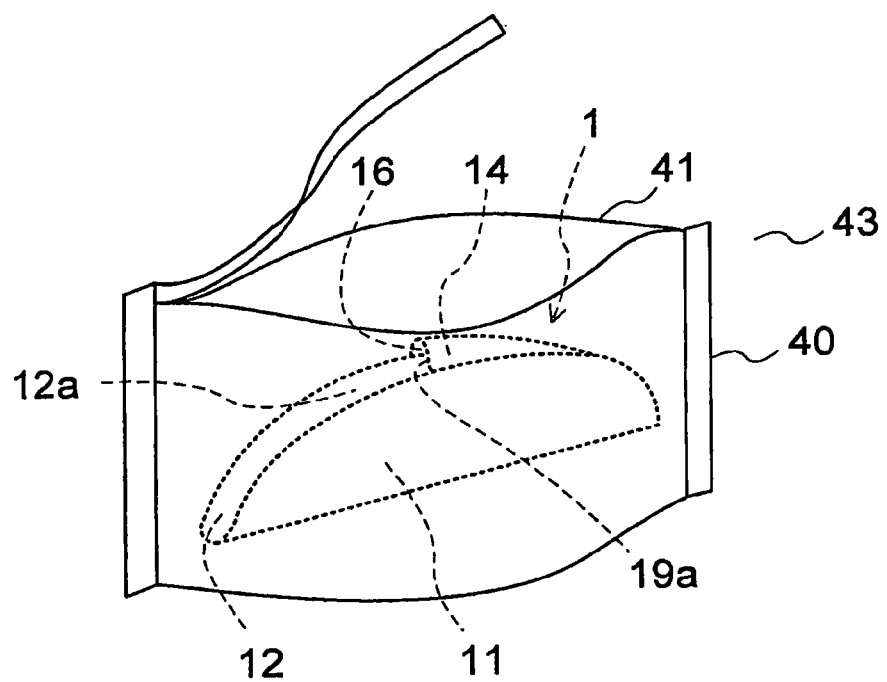
FIG. 12 shows the open state of an individual wrapping body where the interlabial pad according to one embodiment of the present invention is enclosed by folding the back side sheet inside.
Figure 13:
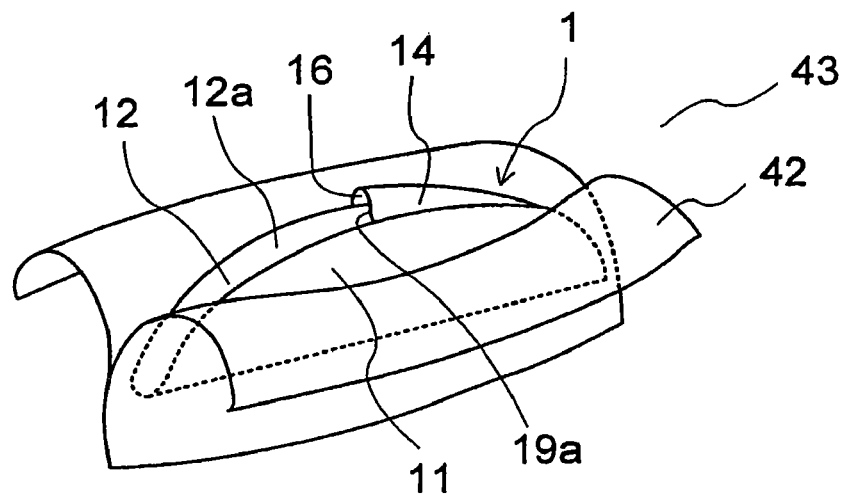
FIG. 13 shows the open state in case where the interlabial pad according to one embodiment of the present invention is enclosed in a wrapping container that opens like the double hinged door.

The interlabial pad produced by affording such a folding habit eases storage, when it is received by a wrapping container and forms the individual wrapping body. FIG. 11 and FIG. 12 show an individual wrapping body 43 containing an interlabial pad 1 in a wrapping container 40. The interlabial pad 1 is stored in the wrapping container 40 in a state being folded in two along the center crease 205, and it is folded in two in a direction where the back side sheet 12 becomes the outside in FIG. 11, and in a direction where the surface side sheet 11 becomes the outside in FIG. 12. The interlabial pad 1 which has a folding habit also has further advantages of not bulky when stored, in addition to being easy to be stored in the wrapping container 40. Especially, it becomes easy to take out the interlabial pad 1 from an unsealing opening 41 of the individual wrapping body 43 and to insert the finger into the pocket 16 through the finger insertion opening 19*a*, when respective folding habit of the mini-sheet piece 14 and the absorbent layer 2 are provided so that they may become opposed in the direction (direction wherein the portion of folding habit of the mini-sheet piece 14 and the portion of folding habit of the absorbent layer 2 separate) as shown in FIG. 12. Moreover, it is easy to open individual wrapping body 43 and to take it out when wrapping container 42 shown in FIG. 13 is used.

Figure 14:
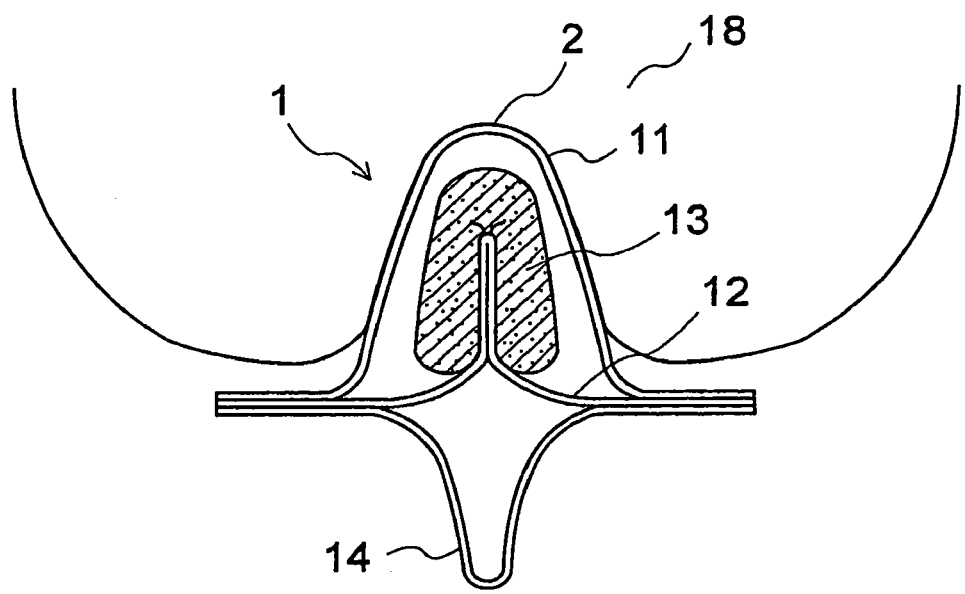
FIG. 14 shows the state where the interlabial pad according to one embodiment of the present invention is fitted between labia.

Moreover, there is also an advantage that it becomes easy to pinch the absorbent layer 2 between labia, as such portion of folding habit becomes a convex area, when the folding habit is formed in the interlabial pad 1, and turns to have a function similar to a convex protruding area 28 in FIG. 16 to be described later. The state of pinching of the absorbent layer 2 between labia 18 is shown in FIG. 14. The absorbent layer 2 of the interlabial pad 1 is pinched by the labia 18, and absorbs the body fluid as shown in FIG. 14.

The Second Method

Figure 15:
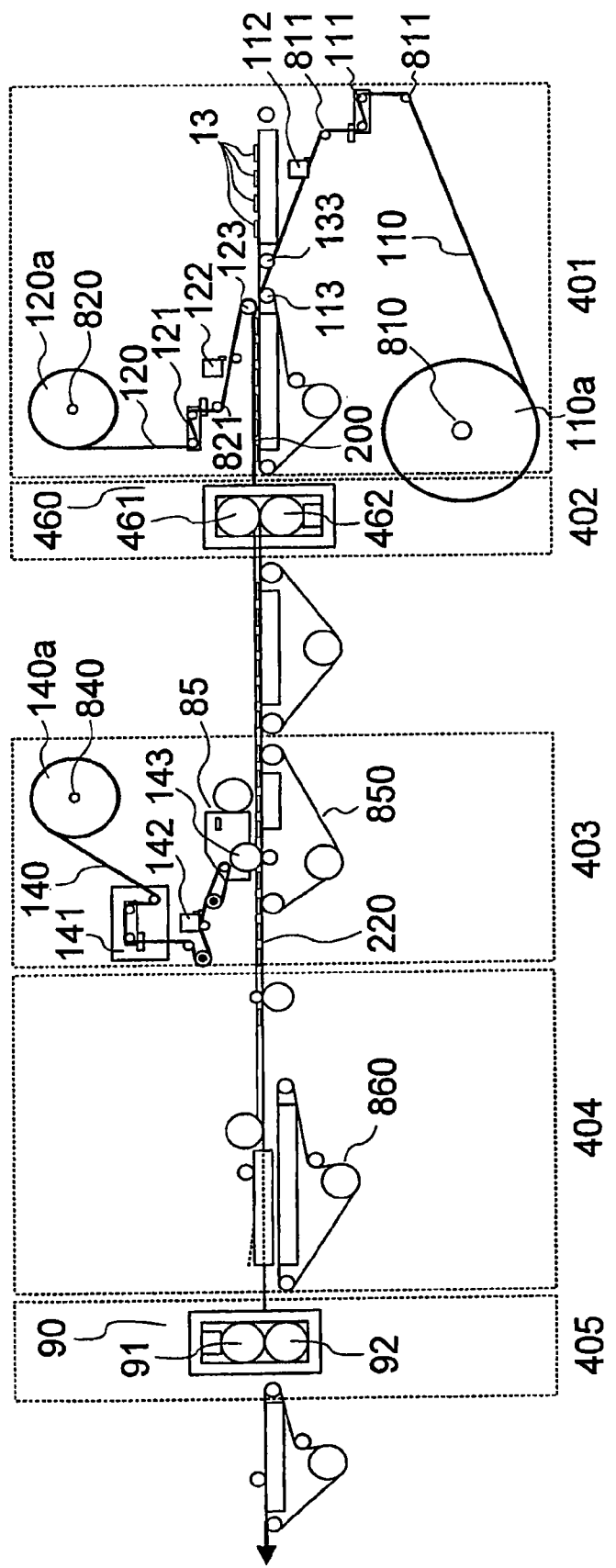
FIG. 15 is a side view where an apparatus for producing interlabial pad in one embodiment according to the present invention is shown.

Subsequently, the second method that is another embodiment of the present invention shall be described. FIG. 15 shows an apparatus for producing a sanitary absorbent article used for the second producing method, comprising a main part assembly unit 401, a joint part regular joining unit 402, a mini-sheet assembly unit 403 and a round cut unit 405 and comprising a folding unit 404 as necessary. The apparatus shown in FIG. 15 has a joint part regular joining unit 402 including a joint part regular joining mechanism 460 behind the main part assembly unit 401. The joint part regular joining mechanism 460 includes an upper roller 461 and a lower roller 462. The same reference numerals in the figure as those of FIG. 10A indicates the same member This second method comprises:
a) a main part assembly step that forms a main part continuous body 200 by arranging a surface side sheet continuous member 110 comprising continuous materials, which form surface side sheets to be positioned on the body side when worn and a back side sheet continuous member 120 comprising continuous materials, which form back side sheets to be positioned on the opposite side to the body side, so as to enclose an absorbent body;

b) a joint part regular joining step that regularly joins the absorbent body 13, the surface side sheet continuous member 110, and the back side sheet continuous member 120 to one body, or the surface side sheet continuous member 110 and the back side sheet continuous members 120 except the absorbent body 13 at a joint part on the surrounding edge of the absorbent body 13;

c) a mini-sheet assembly step that forms a sanitary absorbent article continuous body by spreading temporary joining means such as adhesives to a part or the whole of one of the surface of a mini-sheet piece continuous member 140 comprising continuous materials from which mini-sheet pieces, positioned in contact with back side sheet continuous member 120, separating the mini-sheet piece continuous member into two or more mini-sheet pieces by cutting to a prescribed length on a suction roller 143, and joining the concerned mini-sheet piece to a face that becomes the opposite body side face to body side face of the back side sheet continuous member 120 from the suction roller 143; and d) a round cut step that forms the outer contour of individual interlabial pads by cutting off the sanitary absorbent article continuous body 220 with prescribed width provided from the absorbent body 13.

In the second method, the mini-sheet assembly step is provided after the joint part regular joining step. In the mini-sheet assembly step, a mini-sheet is arranged to the opposite body side face to body side face of the back side sheet continuous member 120 of the main part continuous body 200 and regularly joined to the back side sheet continuous member 120. Therefore, as for the joining of the joint part forming the surrounding of the absorbent body 13 and the mini-sheet joint part, first, the surface side sheet continuous member 110 and the back side sheet continuous member 120 are joined at the joint part regular joining step, and the joint part is formed. The surface side sheet continuous member 110 and the back side sheet continuous member 120 are joined at the joint part by a joint part regular joining mechanism 460 that has an upper roller 461 and an under roller 462, at the joint part regular joining step. At this time, a soft texture of the joint part can be formed, as the mini-sheet piece, surface side sheet continuous member 110, and back side sheet continuous member 120 do not constitute an integrally heat seal joined structure.

Here, a significant difference between the first method and the second method consists in that the joint part and the mini-sheet joint part are joined at the same time in the first method, while in the second method the surface side sheet continuous member 110 and the back side sheet continuous member 120 are joined to form the joint part before the mini-sheet piece is arrange. That is, the surface side sheet continuous member 110, the back side sheet continuous member 120, and the mini-sheet piece are joined all at once in the first method, while the surface side sheet continuous member 110 and the back side sheet continuous member 120 are joined before the mini-sheet piece is arranged in the second method.

It is preferable to install a folding step that folds the sanitary absorbent article continuous body 220 at a center crease provided along a direction where the sanitary absorbent article continuous body 220 is continuous before the round cut step.

Storage of the Interlabial Pad of this Embodiment

It is desirable to store the interlabial pad with the pocket formed by the mini-sheet piece provided in the lateral direction of the absorbent layer in a wrapping container as mentioned above.

FIG. 11 and FIG. 12 are drawings showing the individual wrapping body 43 that stores the interlabial pad 1 in the wrapping container 40. A pocket 16 for finger insertion is located near the unsealing opening 41, as shown in FIG. 11, in the individual wrapping body 43 enclosing the interlabial pad 1 produced by the method of this embodiment, stored in the wrapping container 40 so that the pocket 16 may open naturally. Therefore, the wearer can insert a finger into the pocket 16 at once so that the ball of a finger may bound to the back side sheet 12, as the finger insertion opening 19a opens naturally by the plastic deformation of the mini-sheet piece 14 and the absorbent layer 2 when the wrapping container 40 is unsealed.

In the present invention, it is enough that interlabial pad 1 is located in wrapping container 40 so that the pocket 16 may open near the unsealing opening 41, and in case where the mini-sheet piece 14 is narrower than the width of the absorbent layer 2 as shown in FIG. 12, or in other cases, it may be folded with the back side sheet 12 to the inside.

Moreover, the wrapping container 40 only has to be such a form that a wearer's finger can be inserted at once after the unsealing into the pocket 16 that the interlabial pad 1 possesses. Therefore, for instance, a wrapping container 42 of the shape that becomes gatefold as shown in FIG. 13 may be used.

The Third Method

Subsequently, the third method shall be described. This third method is a method for producing interlabial pad 20 shown in FIG. 16. Before the explanation of this third method, the interlabial pad 20 produced by the third method shall be described, because the interlabial pad 20 is a variant of the interlabial pad 1 shown in FIG. 1 to FIG. 9.

Interlabial Pad Having a Protruding Area

Figure 16:
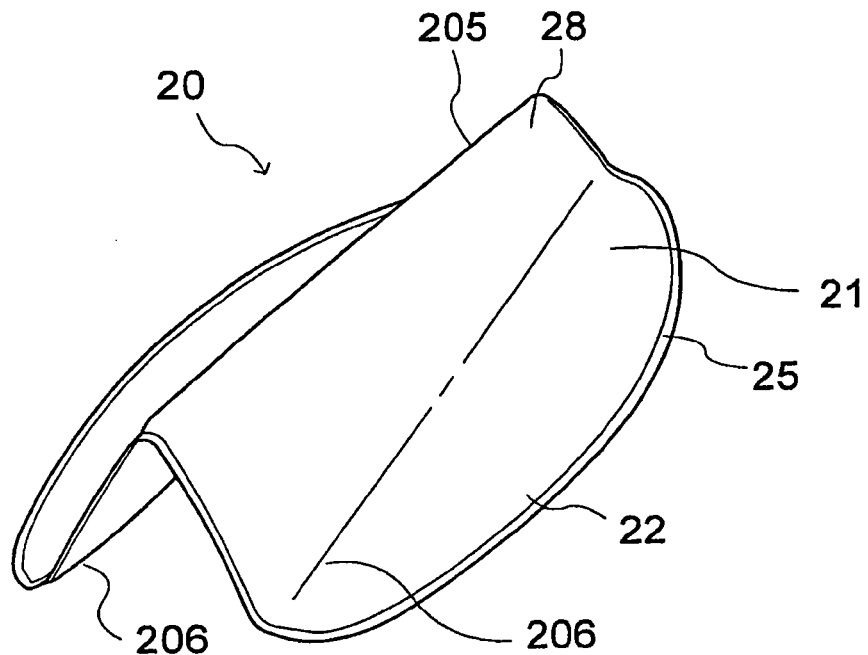
FIG. 16 is a perspective view of an interlabial pad of one embodiment according to the present invention.
Figure 17:
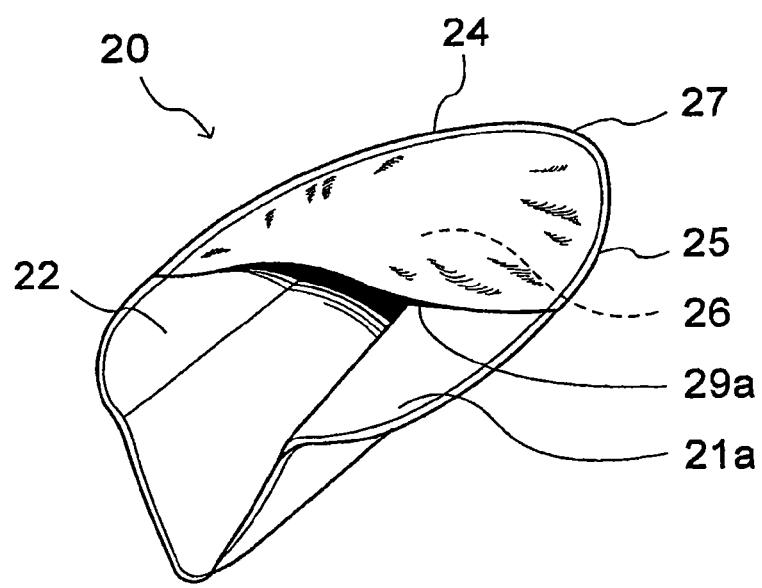
FIG. 17 is a back side view of the interlabial pad of FIG. 16.

The interlabial pad 20 has a protruding area 28 on the body side that becomes convex toward the body, FIG. 16 is a perspective view of the interlabial pad 20, and FIG. 17 is a rear view of interlabial pad 20.

The interlabial pad 20 has an absorbent layer 22 formed by joining at the joint part 25 on the surrounding edge, the surface side sheet 21, the back side sheet 21a, and a not shown absorbent body being pinched, and a pocket 26 is formed by joining the mini-sheet piece 24 to the back side sheet 21a at the mini-sheet joint part 27 provided on the surrounding edge except for the finger insertion opening 29a. Different from the interlabial pad 1 shown in FIG. 1 to FIG. 9, the interlabial pad 20 has a convex protruding area 28 along the longitudinal direction of the surface side sheet 21. And, it is the one that allows enhancing the advantage of the interlabial pad to be closely adhesive, by further improving the adhesion of the wearer's body by forcing such protruding area 28 deep in the wearer's labia. Therefore, the interlabial pad 20 differs remarkably in that it presents the ease of fitting, retention during the wearing, and close adhesion at the same time, from other sanitary articles which may look like similar at the first sight, For instance, the sanitary napkin and so on where only a part of the face being in contact with the body protrudes, as disclosed in the Japan Utility Model Laid Open Publication HEI 5-18523, is different from the interlabial pad 20.

A wearer can adequately know the position in which the protruding area 28 is made to enter into the labia, with the belly of the finger by using the finger inserted into the pocket 26, because it has a structure that allow to insert the finger into the pocket 26 for finger insertion, according to the present invention. That is, it is easy to fit the interlabial pad 20, all the way inserting the protruding area deep into the labia by using a finger inserted into the pocket part 26, as the inside of the pocket 26 and the inside of the concerned protruding area 28 are integrated.

Thus, the convex protruding area 28 can be fixed strongly between the labia by becoming an area that can lie partially between the labia, and it is possible to absorb menstrual blood from the ostium vaginae directly, and it can decrease the possibility that a gap is generated between the surface of the pudenda and the surface side sheets 21, which is water permeable material, in an area that extends right and left in the lateral direction of the protruding area 28. And, the possibility to intercept the leak of menstrual blood flowing in the longitudinal direction of the absorbent layer 22 increases, because it can suppress the generation of the gap between the labia and the interlabial pad 20 as much as possible, and a fear for the menstrual blood outflow from the lateral direction of the absorbent layer 22 can be decreased, because the absorption face of the absorbent layer 22 can be kept substantially vertical for the discharge direction of the menstrual blood flowing rapidly in abundance across the labia inner wall in the direction of the opposite side to the body side.

The Third Method

Figure 18:
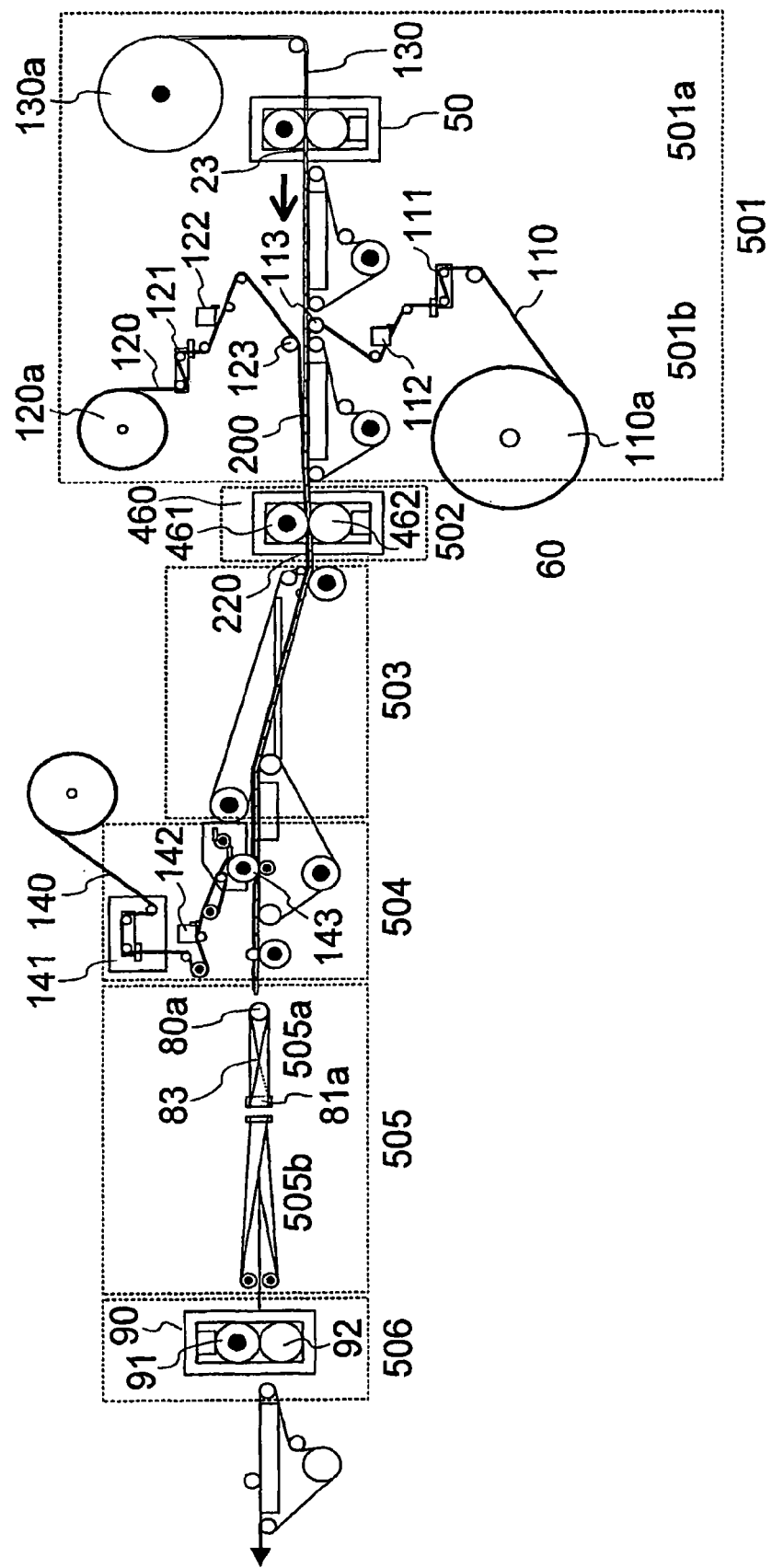
FIG. 18 is a side view where an apparatus for producing interlabial pad in one embodiment according to the present invention is shown.

Hereinafter, a third method shall be described. FIG. 18 shows an apparatus for producing a sanitary absorbent article used for the third producing method, comprising a main part assembly unit 501, a joint part regular joining unit 502, a folding unit 503, a mini-sheet assembly unit 504, a side creases releasing unit 505 and a round cut unit 506. The side creases releasing unit 505 includes a side creases releasing mechanism 505a. The side creases releasing mechanism includes a plurality of third feeding rollers 80a, 81a and a third feeding belt 83. A direction conversion mechanism 505b may be provided in the side creases releasing unit 505 as necessary. The same reference numeral in FIGS. 10A and 15 indicates the same member.

The third method comprises:
  a) a main part assembly step that forms a main part continuous body 200 by arranging a surface side sheet continuous member 110 comprising continuous materials, which form surface side sheets to be positioned on the body side when worn and a back side sheet continuous member 120 comprising continuous materials, which form back side sheets to be positioned on the opposite side to the body side, so as to enclose by interposing an absorbent body 23;
  b) a joint part regular joining step that regularly joins the absorbent body 23, the surface side sheet continuous member 110, and the back side sheet continuous member 120 to one body, or the surface side sheet continuous member 110 and the back side sheet continuous members 120 except the absorbent body 23 at a joint part on the surrounding edge of the absorbent body 23;
  c) a folding step that forms a convex protruding area by folding the main part continuous body 200 to the direction where the back sheet continuous member 120 becomes inside by at a center crease provided along a direction where the main part continuous body 200 is continuous and, at the same time, forms substantially flat drapes at both end parts in a direction orthogonal to the direction where the main part continuous body 200 is continuous, by folding the main part continuous body 200 to the direction where the back side sheet continuous member 120 becomes outside by a pair of side creases provided substantially symmetrical to the center crease;
  d) a mini-sheet assembly step that forms the sanitary absorbent article continuous body 120 by providing a back side sheet side mini-sheet joint part for joining the mini-sheet piece at the drape parts of the back side sheet continuous member 200 of the main part continuous body 200, at the same time providing a mini-sheet piece side mini-sheet joint part for being joined to the back side sheet 120 on the mini-sheet piece cut into a prescribed length, applying adhesives to at least a part of said mini-sheet joint part, and regularly joining the mini-sheet piece and the back side sheet continuous member 120 when the mini-sheet piece is arranged to a side which becomes the opposite body side face to body side of the back side sheet continuous member 120;
  e) a side creases releasing step that restores a portion folded along the side creases; and
  f) a round cut step that produces each interlabial pad 20 by cutting off the sanitary absorbent article continuous body 220 in a state where said sanitary absorbent article continuous body is folded along the center crease.

In the concerned method, the length of the main processing process (absorbent body cutting~round cut) has been remarkably shortened compared with the sanitary napkin of the prior art (concretely, the length of apparatus used on main processing process of the interlabial pad is about 5 m, while the length of apparatus used on main processing process of the sanitary napkin is about 20 m). The shortening of this producing process is performed by shortening the raw material feeding process. That is, in the sanitary napkin producing of the prior art, it was given priority to the improvement of operationality by the arrangement of respective materials near the worker, because the arrangement of materials is executed by the operator's manual procedures, while the shortening of the delivery distance of the raw material was not valued so much. Moreover, there was another inconvenience that the sanitary napkin is composed of a number of members (The number of elements of the sanitary napkin is about 20, while the number of elements of the interlabial pad is about 10), making the shortening of the producing process more difficult.

Moreover, the sanitary napkin does not come in contact with the mucous membrane, because the sanitary napkin is not the one to be pinched between labia when wearing, and even if the seal position to the absorbent body position of each element and the cutting position is dislocated in the course of a long producing process, the wearing feeling was not influenced adversely, by setting a large design tolerance, without any particular inconvenience.

However, the wearing feeling might be immediately influenced harmfully, when the interlabial pad is produced with the gap of seal position or cutting position to the absorbent body position of each element, because the interlabial pad is the one to be used by placing it between the labia. For instance, when room is given to the pinching margin (surroundings edge portion that becomes the selvage of the absorbent layer) to hold the enclosed absorbent body, this portion causes to stimulate the wearer's mucous membrane when wearing it. In a word, even if it is the same degree of gap as the sanitary napkin, the extent of its influence becomes considerably large in the interlabial pad with small size compared with the sanitary napkin.

In view of such inconveniences, in the present invention, more importance is attached to the wearing feeling of the finished product that the operationality in the producing process, main processing process is shortened, and more concretely, those not to be processed (raw fabric) are made to be transported form a remote point, and after the combination, processing points are disposed in the proximity to intend to shorten the feeding process, and it is the one that allows producing an interlabial pad of a suitable wearing feeling and saving space of the producing apparatus, by decreasing the generation of gap to be caused in the producing process.

Hereafter, a third embodiment that produces the interlabial pad 20 of FIG. 16 that is one embodiment of the present invention, referring to FIG. 18.

Main Part Assembly Step

First of all, the step for supplying raw material shall be described. The surface side sheet continuous member 110 is drawn out from a raw fabric roll 110*a* of surface sheet continuous member, passed through a first meander correcting mechanism 111, and sent to a first hot melt type adhesive spreading mechanism 112. A surface side sheet side joint part is provided in a portion where the surface side sheet and the back side sheet are joined on the surface side sheet continuous member 110. And, the surface side sheet continuous member 110 is sent to pass over the assembling roller 113 after the first hot melt type adhesive spreading mechanism 112 has continuously supplied the hot melt type adhesive to the surface side sheet side joint part of the surface side sheet continuous member 110.

On the other hand, the back side sheet continuous member 120 is drawn out from a raw fabric roll 120*a* of back sheet continuous member, passed through a second meander correcting mechanism 121, and sent to a second hot melt type adhesive spreading mechanism 122. A back side sheet side joint part is provided in a portion where the surface side sheet and the back side sheet are joined on the back side sheet continuous member 120. And, the back side sheet continuous member 120 is sent to pass under the assembling roller 123 after the second hot melt type adhesive spreading mechanism 122 has continuously supplied the hot melt type adhesive to the back side sheet side joint part of the back side sheet continuous member 120.

Besides, a continuous absorbent body 130 formed with absorbent bodies continuously is drawn out from a raw fabric roll 130*a* of absorbent body, and cut into an individual absorbent body 23 by a cutting absorbent body cutting mechanism 50. Then, it is sent between assembling rollers 113 and 123, and arranged between the surface side sheet continuous member 110 and the back side sheet continuous member 120 to form the main part continuous body 200.

Figure 19:
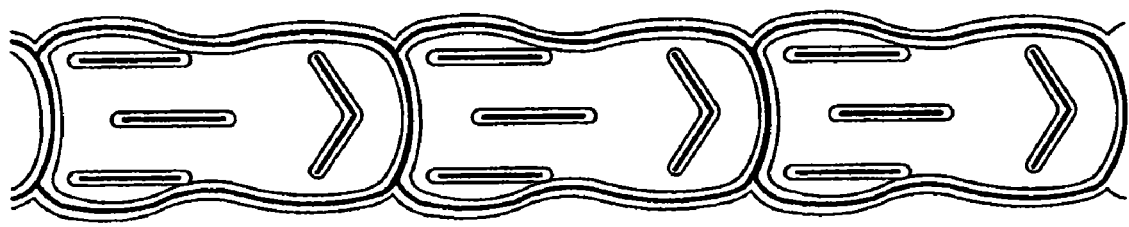
FIG. 19A shows incisions to be cut in the absorbent body.
FIG. 19B shows incisions to be cut in the absorbent body.
Figure 19:
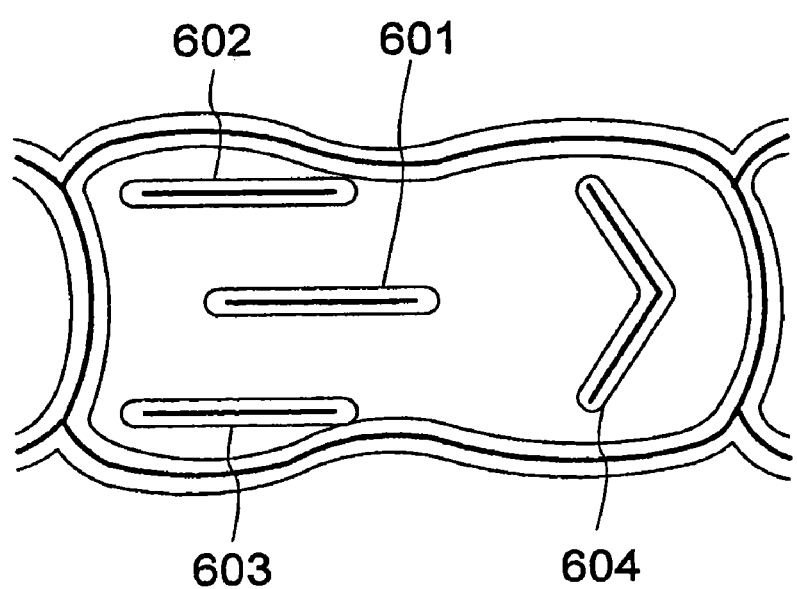

In this embodiment, a prescribed incision is cut in the absorbent body 23. FIG. 19 is a drawing where the incision of the absorbent body 23 is shown, and four incisions are cut at the same time as shown in FIG. 19A. Now, such incision shall be described according to the number shown in FIG. 19B: the first incision line 601 is provided to make the absorbent body 23 easy to be folded (it is beneficial at the time of folding), the second incision line 602 and the third incision line 603 are provided to make the mini-sheet piece easy to attach (it is beneficial to attach the mini-sheet), and the fourth incision line 604 is provided to make the wearer's finger and the interlabial pad affinitive during the wearing, respectively.

The hot melt type adhesive used in the main part assembly step in this embodiment is a mean to join temporarily the surface side sheet continuous member 110 and the back side sheet continuous member 120. Therefore, the hot melt type adhesive only has to be spread at least on a part of the surface side sheet side joint part or the back side sheet side joint part, and the hot melt type adhesive has not to be applied on either of the surface side sheet continuous member 110 or the back side sheet continuous member 120.

The hot melt type adhesive mentioned above is the one generally used as so-called hot melt applicator. Concretely, the hot melt type adhesive is melted by heating it in a not shown melting tank, sent forcefully to a supply hose with various pumps such as gear pump, plunger pump, or the like and the hot melt type adhesive sent in the manifold is discharged under pressure from a nozzle of a prescribed shape. The spreading pattern of this hot melt type adhesive can arbitrarily have shapes of the line, plane, spiral, omega in the upper case character, mist, reticulation, and so on, and a pressure sensitive hot melt type adhesive heated in the range of 120 degree Celsius to 180 degree Celsius is applied in the range of 1 to 10 g/m$^2$ by a specific weight per unit.

Joint Part Regular Joining Step

Subsequently, a joint part regular joining step joins the surface side sheet continuous member 110 and the back side sheet continuous member 120 shall be described.

The absorbent body 23 is supplied to be arranged between the surface side sheet continuous member 110 and the back side continuous sheet continuous member 120, and is supplied matching with the timing of the supply of the surface side sheet continuous member 110 and the back side sheet continuous member 120. The main part continuous body 200 that consists of the surface side sheet continuous member 110, the back side sheet continuous member 120, and the absorbent body 23 arranged between both sheet continuous members is passed between an upper axial roller 461 and an lower axial roller 462 of a joint part regular joining mechanism 460, and a joint part of the interlabial pad is formed, by joining the surface side sheet continuous member 110 and the back side sheet continuous member 120 around the surrounding edge of the absorbent body 23 by pressing from the upper side and the lower side with a pressurizing mechanism provided on the upper axial roller 461 and the lower axial roller 462.

The upper axial roller 461 constitutes a smooth surface shape, while the lower axial roller 462 is provided with a emboss pattern arranging emboss parts in 3 rows with an angle of 45°, emboss parts being adjacent by 0.7 mm$^2$ for each corner, and leaving an interval of 1 mm between the adjacent emboss parts. And, the upper axial roller 461 has heat in the range of 70 degree Celsius to 120 degree Celsius and the lower axial roller 462 in the range of 90 degree Celsius to 140 degree Celsius respectively, and they are adjusted to have a line pressure of 300000 to 900000 N/m, to perform a joining by heat seal.

Folding Step

Figure 20:
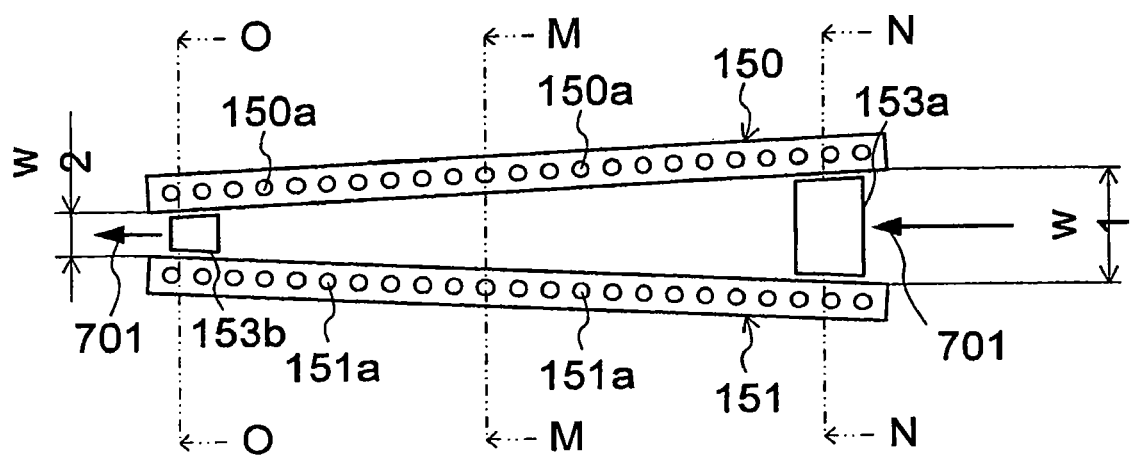
FIG. 20A is a top view of the folding unit of FIG. 18.
FIG. 20B is a side view of the folding unit of FIG. 18.
FIG. 20C is a cross section view of the N-N section of FIG. 20A.
FIG. 20D is a cross section view of the M-M section of FIG. 20A.
FIG. 20E is a cross section view of the O-O section of FIG. 20A.
Figure 20:
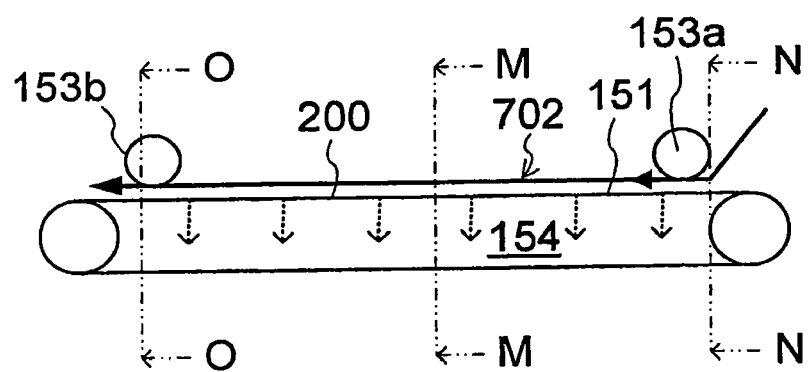
Figure 20:
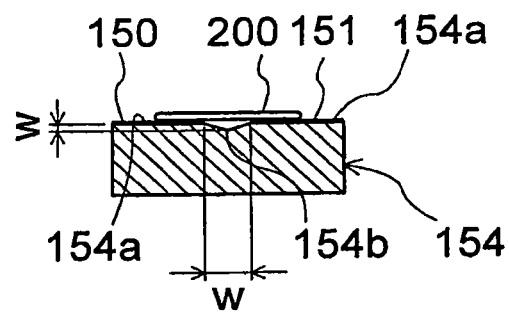
Figure 20:
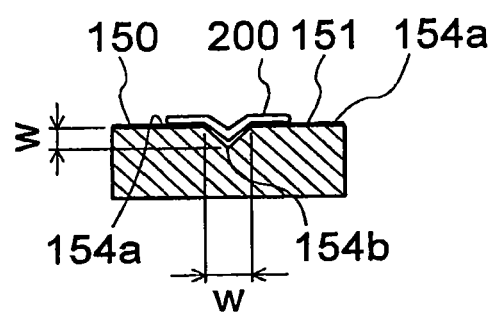
Figure 20:
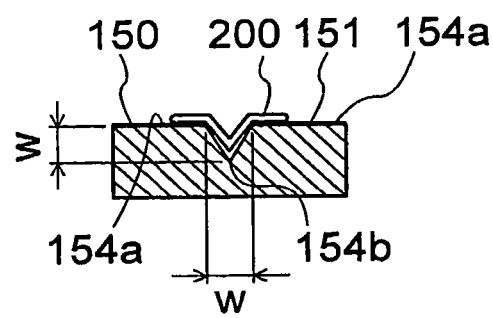

Subsequently, a folding step that forms the protruding area shall be described. FIG. 20A shows the state of the folding unit 503 viewed from above, FIG. 20B shows the approaching sate of the main part continuous body 200, FIG. 20C is the cross-section along N-N section of FIG. 20A, FIG. 20 D is the cross-section along M-M section of FIG. 20A, and FIG. 20 E is the cross-section along O-O section of FIG. 20A, respectively.

The apparatus shown in FIG. 18 has a main part assembly unit 501, a joint part regular joining unit 502, a folding unit 503, a mini-sheet assembly unit 504, a side creases releasing unit 505, a round cut unit 506 in this embodiment from right to left. In case of the third production method, production step for sanitary absorbent article proceeds in the direction from right to left, the main part continuous body 200 is transformed like V-shape in the folding step as the main part continuous body 200 progresses according to this proceeding direction. As a result, in the absorbent layer of the interlabial pad, as a finished product, a center crease and a pair of side creases to be provided substantially symmetrical to the center crease are afforded, to form a protruding area. When FIG. 16 is referred, the protruding area 28 is a convex part that presents a reverse-V-shape having the center crease 205 as a point, in a cross-section in the lateral direction of absorbent layer 22 when surface side sheet 21 is taken as the upper surface, and that is delimited by a pair of side creases 206 provided substantially symmetrical to the center crease 205. In this embodiment, it is molded so that ups and downs of the protruding area 28 may gradually grow in the folding unit 503.

To be specific, a pair of second feeding belts 150 and 151 are arranged in such a way to be opposed, along the proceeding direction of the production line (direction indicated by the arrow 701) as shown in FIG. 20A. These both second feeding belts 150 and 151 are located to have an interval becoming gradually narrower from the upstream toward the downstream of the proceeding direction. (w1>w2).

Then, under the second feeding belt 151, a guide 154 that has a smooth part 154a and a V-shape ditch part 154b as shown from FIG. 20C to FIG. 20 E is continuously arranged along the proceeding direction of the production line as shown in FIG. 20B. The main part continuous body 200 moves on the guide 154 with the surface side sheet continuous member 110 below and the back side sheet continuous member 120 above, and the smooth part 154a rotates to send off the main part continuous body 200 to the proceeding direction at the same speed.

A suction hole (not shown in the drawing) has been provided in this smooth part 154a. And, holes 150a and holes 151a of the hole diameter 3 to 15 mm have been provided in the second feeding belt 150 and the second feeding belt 151 distributed on such smooth part 154a at an interval of 5 to 30 mm, in a way to correspond to the suction hole of the smooth part 154a.

The smooth part 154a transports the main part continuous body 200 to the proceeding direction, while maintaining the mini-sheet joint part in a flat state to join the mini-sheet piece to the main part continuous body 200 by a suction pressure of 1500 to 3000 Pa from the not shown suction hole of the guide 154, through the second feeding belt 150 and 151 having holes 150a and 151b. By doing like this, it is enable to transport the main part continuous body 200 in V, while securing the mini-sheet joint part where the mini-sheet piece is joined in the smooth part 154a. with the main part continuous body 200 folded.

Here, the width of the smooth part 154a is adjusted in the range of 20 to 40 mm, because it is necessary to keep it flat as a stand for joining the mini-sheet piece to the back side sheet continuous member 120 of the main part continuous body 200.

The ditch depth of V-shape ditch 154b (distance from the smooth part 154a to the point of the V-shape ditch 154b) and the width of the ditch are not constant as shown from FIG. 20C to FIG. 20 E. Concretely, the ditch depth is formed in the range of 15 to 30 mm, the width w of the ditch of the V-shape ditch 154b is formed in the range of 35 to 50 mm at the entrance position of the folding unit (refer to FIG. 20C) and in the range of 15 mm to 25 mm at the exit position (refer to FIG. 20E).

Sliding Guide

In this embodiment, from the structure as mentioned above, both side portions of the main part continuous body 200 that flows on the second feeding belts 150 and 151 are lifted up under the influence of suction, and the center portion of the main part continuous body 200 free from the influence of suction pressure tends to keep an untouched position, providing consequently a center crease along the direction where the main part continuous body 200 is continuous (direction of the arrow 701 in FIG. 20A), and a portion that becomes the protruding area of the interlabial pad that presents a substantially V shaped having the surface side sheet continuous member 110 as the lower side is formed on the main part continuous body 200.

In this embodiment, in addition to this, a disk like guide 153a for entrance and a guide 153b for exit are provided as a sliding guide for pressing the main part continuous body 200 in the depth of the V-shape ditch 154b of the guide 154, so that that the main part continuous body 200 is folded more surely.

These guide 153a for entrance and guide 153b for exit are the rotation bodies. And, the guide 153b for exit is a driving roll, while the guide 153a for entrance is a free roll (roll that turns in the force of materials). This is because the main part continuous body 200 can be sent without being stuck in an exit this off by the driving power of the guide 153b for exit, because the width between the second feeding belts 150 and 151 narrows gradually as mentioned above.

The aforementioned guide 153a for entrance and guide 153b for exit are subjected to such a treatment by which the main part continuous body 200 may slide easily thereon. This is because, though a comparatively small size roller is used in this embodiment because the producing process is short, such roller entraps the raw material easily, and the surface of the roller should be made slippery for materials, to prevent this roller from trapping the raw material The guide 153a for entrance restricts the folding direction to make the main part continuous body become convex on the surface sheet side. Moreover, the guide 153b for exit can impart a constant height by thrusting to the depth of deformation height of the product from the surface of the feeding belts 150, 151. The main part continuous body 200 can surely be folded by making it passed in this manner. Moreover, because both guides of 153a and 153b are arranged between the second feeding belts 150 and 151, the main part continuous body 200 comes to be fixed on the second feeding belts 150 and 151, and the main part continuous body 200 can be folded in a stable state compared with the case of arranging the concerned guide in other places (for instance, before the feeding belt).

In this embodiment, the base point to fold at the center crease is kept on the central line of the product, and the fold position can be made constant all the time, by providing folding habit step to make a folding habit such as a pause line, a broken line, a compression line and so on, in respect to the center crease of the main part continuous body 200, between the main part assembly step and the joint part regular joining step, before the folding step. It becomes possible to give the chance that the main part continuous body 200 deforms easily in conformity with the V-shape ditch 154b and to decrease the generation of distortion or the like, by forming such habit of folding.

For instance, the pause line can be processed by the rotary cutter having a blade, which is provided consecutively in the straight line in the proceeding direction of the production line, and the compression line can be processed by a so-called rotary cutter and so on adjusted to have a line pressure of 300000 to 900000 N/m along the center crease of the absorbent layer, which is continuously fed by the roller provided with a convex portion having a width of 0.5 to 3 mm in width.

In addition, a folding step can include a finger insertion restriction part forming unit that forms a finger insertion restriction part made by joining the opposite body side face to body side faces of the back side sheet each other to prevent the finger inserted too much into the pocket from the finger insertion opening, in a forward portion of the interlabial pad (part that corresponds to the clitoris neighborhood when wearing it).

Figure 21:
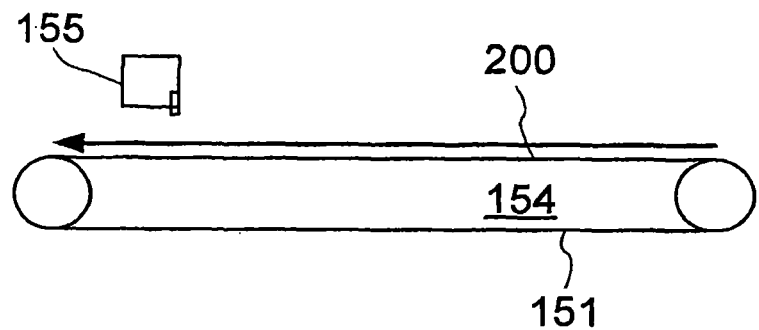
FIG. 21 shows a formation unit of finger insertion restriction part.

FIG. 21 shows the finger insertion restriction part forming unit, and concretely, a hot melt adhesive spreading apparatus 155 is arranged for spreading the adhesive in the vicinity of the center crease of the back side sheet continuous member of the main part continuous body 200. And, the back side sheet continuous member 120 in the vicinity of the concerned center crease is joined each other with the adhesive spread on the back side sheet continuous member 120.

The hot melt adhesive type adhesive is the one generally used as so-called hot melt applicator, the hot melt type adhesive is melted by heating it in a not shown melting tank, sent forcefully to a supply hose with a gear pump, and the hot melt type adhesive sent in the manifold is discharged under pressure from a nozzle of a prescribed shape. The spreading pattern of this hot melt type adhesive can arbitrarily adopt the line, plane, spiral, omega in the upper case character, mist, reticulation, and so on, and a pressure sensitive hot melt type adhesive heated in the range of 140 degree Celsius to 180 degree Celsius is applied intermittently at the width of 3 to 10 mm in the range of 5 to 50 g/m$^2$ by a specific weight per unit to the vicinity of the edge part of the back side sheet continuous member 120 where a mini-sheet piece is attached.

Mini-Sheet Assembly Step

Subsequently, a mini-sheet assembly step that arranges the mini-sheet piece on the back side sheet continuous member and joins both of them shall be described.

The mini-sheet piece continuous member 140 is drawn out from the raw fabric roll 140a of mini-sheet, sent to the third hot melt type adhesive spreading mechanism 142 passing through the third meander correcting mechanism 141, and hot melt type adhesive is spread at least in a part of the mini-sheet side mini-sheet joint part provided to join the mini-sheet piece to the back side sheet continuous member 120.

Figure 22:
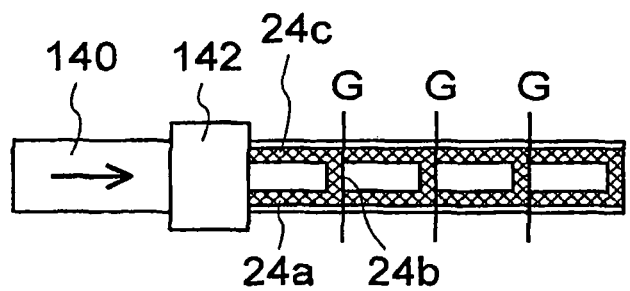
FIG. 22A is a schematic view that shows the coating position of a hot melt type adhesive to the mini-sheet piece.
FIG. 22B is a schematic view that shows the coating position of a hot melt type adhesive to the mini-sheet piece.
Figure 22:
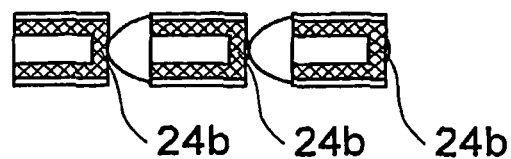

In this case, the finger insertion restriction part may be formed by widening a part of the mini-sheet joint part. FIG. 22 shows the case of forming finger insertion restriction part at the same time as the hot melt type adhesive is spread on the mini-sheet piece continuous member 140. It is possible to form the mini-sheet joint part and the finger insertion restriction part by spreading the hot melt type adhesive continuously or intermittently as shown in FIG. 22A to the mini-sheet side mini-sheet joint part 24a, 24b, and 24c of the mini-sheet piece 24. Concretely, by enlarging width 24w of the 24b portion when the hot melt type adhesive is spread on each position of the mini-sheet side mini-sheet joint part 24a, 24b, and 24c between the cutting planed position GG, the portion of 24b becomes the mini-sheet joint part and the finger insertion restriction part, when the mini-sheet piece continuous member 140 is cut into the individual mini-sheet piece 24, as shown in FIG. 22 B.

The mini-sheet piece continuous member 140 to which the hot melt type adhesive has been applied is maintained on a suction roller 143 by applying a suction pressure by suction from the inside on the concerned suction roller 143 provided with two or more holes, and cut as it is into a prescribed length by a cutter roller having a cutting blade.

The mini-sheet piece cut into the prescribed length is arranged in opposition to the back side sheet continuous member 120, and the mini-sheet piece and the back side sheet continuous member are joined with the hot melt type adhesive spread beforehand, for forming the sanitary absorbent article continuous body 220. In this case, in order to prevent the wrinkle being caused in the finished product, the speed at which main part continuous body 200 is transported is set equal to the speed at which the cut mini-sheet pieces are dropped.

In this embodiment, the sanitary absorbent article continuous body 220 is formed by arranging the mini-sheet piece on the back side sheet continuous member 120, because the mini-sheet piece are regularly joined to the back side sheet continuous member 120 at the same time the mini-sheet piece is arranged on the opposite body side face to body side face of the back side sheet continuous member 120.

Side Creases Releasing Step

Figure 23:
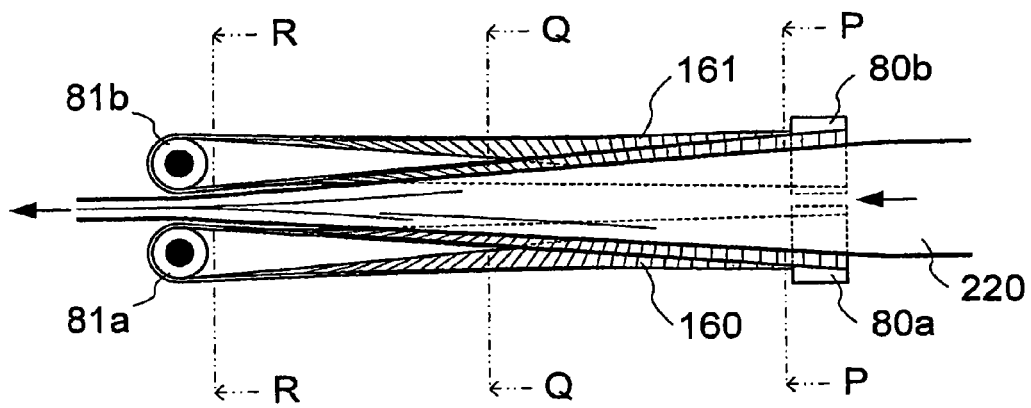
FIG. 23A is a top view of a fold release equipment of FIG. 18.
FIG. 23B is a side view of a fold release equipment of FIG. 18.
FIG. 23C is a cross section view of a sanitary absorbent article continuous body in the P-P section of FIG. 23A.
FIG. 23D is a cross section view of a sanitary absorbent article continuous body in the Q-Q section of FIG. 23A.
FIG. 23E is a cross section view of a sanitary absorbent article continuous body in the R-R section of FIG. 23A.
Figure 23:
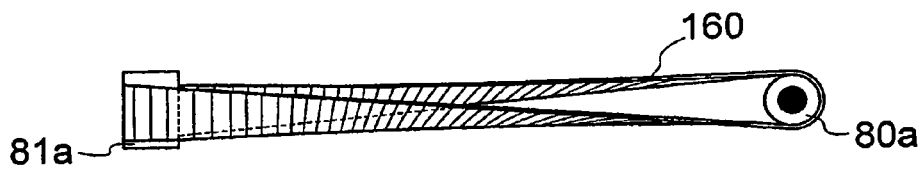
Figure 23:
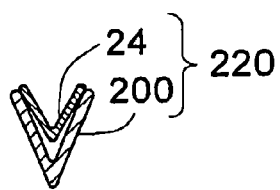
Figure 23:
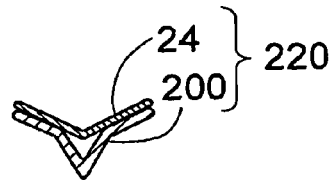
Figure 23:
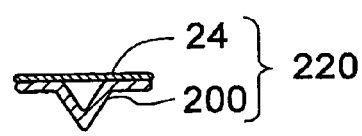
Figure 24:
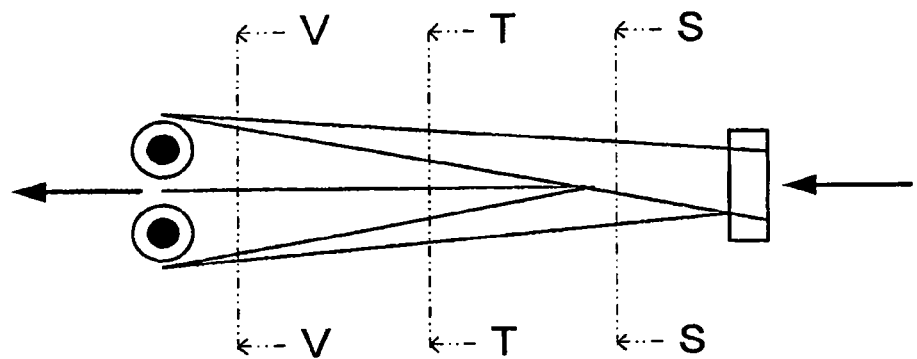
FIG. 24A is a side view of a turnabout apparatus of FIG. 18.
FIG. 24B is a cross section view of a sanitary absorbent article continuous body in the S-S section of FIG. 24A.
FIG. 24C is a cross section view of a sanitary absorbent article continuous body in the T-T section of FIG. 24A.
FIG. 24D is a cross section view of a sanitary absorbent article continuous body in the U-U section of FIG. 24A.
Figure 24:
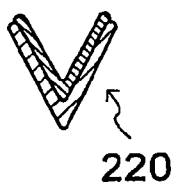
Figure 24:
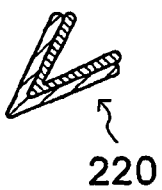
Figure 24:
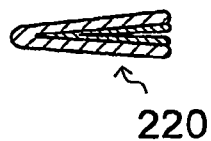
Figure 25:
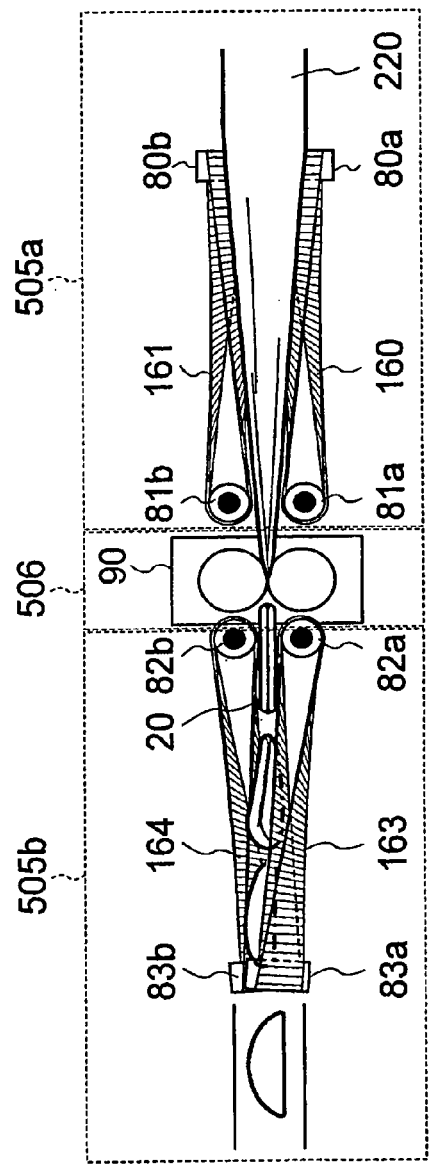
FIG. 25A is a top view of a crease release apparatus, a round cut unit and the turnabout apparatus of a variant of the producing apparatus of FIG. 18 where the turnabout apparatus is installed in a round cut unit rear stage.
FIG. 25B is a view where
Figure 25:
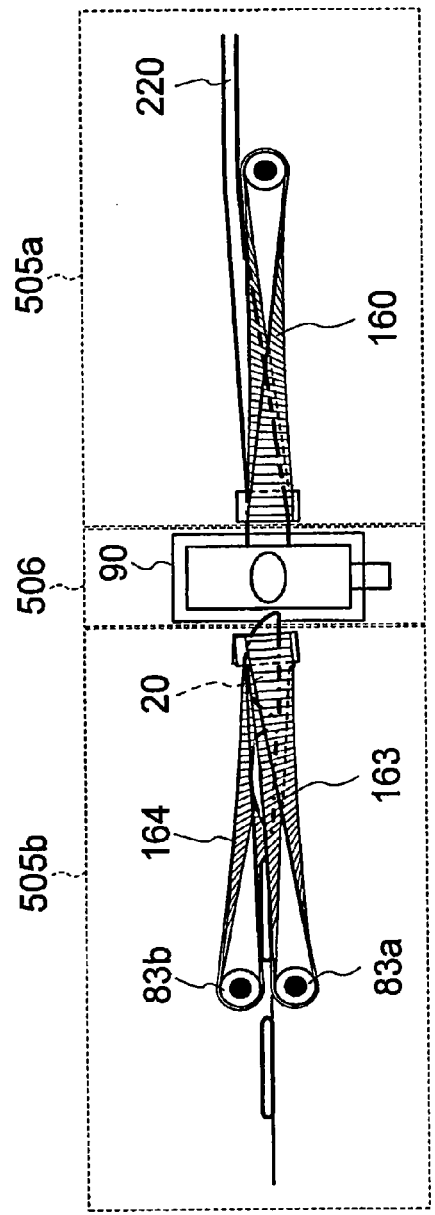

Subsequently, a side creases releasing step that restores a portion folded along the side creases, and at the same time, folds the sanitary absorbent article continuous body 220 in two. The side creases releasing unit 505 shown in FIG. 18 includes a side creases releasing mechanism 505a and a direction conversion mechanism 505b to be described later. FIG. 23 shows the side creases releasing mechanism 505a of comprising the side creases releasing unit 505, FIG. 24 shows the direction conversion mechanism 505b, FIG. 25A is a top view of a variant where the direction conversion mechanism 505b installed in the round cut unit rear stage, and FIG. 25 B is the side view thereof.

The sanitary absorbent article continuous body 220 is in the state folded along the center crease and a pair of side creases, but the mini-sheet piece provided on the main part continuous body 200 is not folded. Therefore, the sanitary absorbent article continuous body 220 is supplied to side creases releasing step with only the main part continuous body 200 being folded.

FIG. 23A is a top view of the side creases releasing mechanism 505a, and a pair of third feeding belts 160 and 161 is arranged in a way to be opposed, toward the proceeding direction of the production line (direction of the arrow). These both third feeding belts 160 and 161 are located in a twisted state by 90° from the upstream toward the downstream of the production line to become gradually vertical from the horizontal. That is, the sanitary absorbent article continuous body 220 transported on these both belts comes to be folded from both sides, because the third feeding belts 160 and 161 are twisted in a way to get up from both sides.

More concretely, a roller 80a is allotted under the third feeding belt 160 at the entrance of the side creases releasing mechanism 505a, and a roller 80b is allotted under the third feeding belt 161. And, a roller 81a and a roller 81b are arranged to become right-angled to the roller 80a and roller 80b at the exit of the side creases releasing mechanism 505a, and twisted so that both third feeding belts 160 and 161 may rotate by 90° compared with the state at the entrance of the fold release equipment 505a. This side creases releasing mechanism 505a becomes as shown in FIG. 23 B when viewed from the side. FIG. 23 C is a cross section of the sanitary absorbent article continuous body 220 in the P-P section of FIG. 23A, FIG. 23 D is a cross section of the sanitary absorbent article continuous body 220 in the Q-Q section of FIG. 23A, and FIG. 23 E is a cross section of the sanitary absorbent article continuous body 220 in the R-R section of FIG. 23A. The sanitary absorbent article continuous body 220 that flows on the third feeding belts 160 and 161 enters the two-folded state gradually along a center crease, as a pair of side creases are released, as shown from FIG. 23C to FIG. 23 E.

FIG. 24A is a side view of direction conversion mechanism 505b, FIG. 24B, FIG. 24C and FIG. 24 D are cross sections of the sanitary absorbent article continuous body 220 in the S-S section, the T-T section, and the U-U section respectively of the FIG. 24A.

Though the sanitary absorbent article continuous body 220 folded into the two-folded state by the side creases releasing mechanism 505a turns to the vertical direction at the terminal part of the side creases releasing mechanism, the direction is changed to turn to the horizontal direction as shown from FIG. 24 B to FIG. 24 D, by the direction conversion mechanism 505b, and it is transported to the round cut step.

The direction conversion mechanism 505b can be provided in the round cut step for doing round cutting rear stage. FIG. 25A is a top view of the side creases releasing mechanism 505a, round cut unit 506, and direction conversion mechanism 505b and FIG. 25 B is a side view of FIG. 25A. The cutting mechanism 90 in FIG. 25 is a round cutter, and it is arranged in the vertical direction. This cutting mechanism 90 is capable of cutting off the sanitary absorbent article continuous body 220 keeping it in the vertical state and making the individual pad horizontal, by transporting thus cut interlabial pad which is an individual product by pinching between the third feeding belts 163 and 164 twisted to change the direction by 90 degree at the entrance and exit of the direction conversion mechanism 505b.

Round Cut Step

Subsequently, a round cut step that cuts off the sanitary absorbent article continuous body 220 shall be described.

The sanitary absorbent article continuous body 220 is cut in the two-folded state by the cutting mechanism 90 in the round cut unit. The cutting apparatus 90, wherein the under roller becomes a receiving roller 92 that has a flat shape, cuts off the sanitary absorbent article continuous body 220 on the outside edge of the joint part by applying pressure to the upper roller 91 which is a cutter roller having a cutter blade, and round cuts portions unnecessary for the structure of the interlabial pad as the finished product. The sanitary absorbent article continuous body 220 is divided into the interlabial pad by each unit of one product where a smooth and round outer contour is formed, by passing this cutting mechanism 90.

The round cut comes to be performed in this two-folded state, as the sanitary absorbent article continuous body 220 is folded in two before cutting. In this respect, if a convex type product is cut keeping it in the plane state, the center portion becomes thick as the absorbent body is folded in V, and each element is crushed. The section of the cutting portion cut in such a state does not become smooth but becomes like the blade of a saw, and deprives the wearing feeling remarkably. Then, an accurate cutting can be done by folding in two before cutting, like this embodiment, regardless of the existence of the enclosed absorbent body.

The individual interlabial labia completed in this manner is shipped after the processes of wrapping, packing, and so on.

What is claimed is:

1. An apparatus for producing an interlabial pad, the apparatus comprising:
   a main part assembly unit comprising:
   a mechanism configured to supply a continuous absorbent body;
   a mechanism configured to cut the continuous absorbent body into individual absorbent bodies;
   a mechanism configured to supply a surface side sheet continuous member;
   a mechanism configured to supply a back side sheet continuous member;
   a mechanism configured to arrange one of the individual absorbent bodies between the surface side sheet continuous member and the back side sheet continuous member; and
   a mechanism configured to assemble a main part continuous body by joining the surface side sheet continuous member and the back side sheet continuous member;
   a mini-sheet assembly unit comprising:
   a mechanism configured to arrange a mini-sheet piece on the back side sheet continuous member of the main part continuous body, and
   a mechanism configured to form an interlabial pad continuous body while forming a finger insertion opening configured to permit insertion of a finger between the back side sheet and the mini-sheet piece by temporarily joining the back side sheet continuous member and the mini-sheet piece, wherein the mechanism configured to cut the continuous absorbent body includes:
   a cutting device configured to form a plurality of incisions in the individual absorbent bodies before placing the individual absorbent bodies between the surface side sheet continuous member and the back side sheet continuous member,
   the cutting device comprising:
   a first cutting device configured to make a first incision line at a center of the individual absorbent bodies;
   a second and a third cutting device configured to make a second and a third incision lines on opposing sides of the first incision line, wherein the first, second and third incision lines are formed along a longitudinal direction of the individual absorbent bodies,
   a fourth cutting device configured to make a fourth incision line as V-shaped with a center point of the V-shaped incision protruding toward a longitudinal end of the individual absorbent bodies.

2. The apparatus for producing an interlabial pad according to claim 1, wherein;
   the mechanism configured to supply a surface side sheet continuous member comprises:
   a first rolling roller configured to roll a raw fabric roll of a surface side sheet,
   a first drawing roller configured to draw the raw fabric roll of a surface side sheet,
   the mechanism of supplying a back side sheet continuous member comprises:
   a second rolling roller configured to roll a raw fabric roll of a back side sheet,
   a second drawing roller configured to draw the raw fabric roll of a back side sheet,
   the mechanism of supplying a mini-sheet piece comprises:
   a third rolling roller configured to roll a raw fabric roll of a mini-sheet,
   a third drawing roller configured to draw the raw fabric roll of a mini-sheet, the mechanism of attaching a mini-sheet comprises:
   a plurality of first feeding rollers, and:
   a suction roller.

3. The apparatus for producing an interlabial pad according to claim 1 further comprising:
   a concurrent regular joining unit configured to regularly join at least the surface side sheet continuous member and the back side sheet continuous member and at the same time regularly join the back side sheet continuous member and the mini-sheet piece.

4. The apparatus for producing an interlabial pad according to claim 3, wherein the concurrent regular joining unit comprises:
   a concurrent regular joining upper roller and
   a concurrent regular joining lower roller.

5. The apparatus for producing an interlabial pad according to claim 1, further comprising:
   a folding unit configured to fold the main part continuous body or the interlabial pad continuous body at a center crease along a direction where the main part continuous body or the interlabial pad continuous body is continuous.

6. The apparatus for producing an interlabial pad according to claim 5, wherein the folding unit comprises a plurality of second feeding rollers.

7. The apparatus for producing an interlabial pad according to claim 5, further comprising:
   a round cut unit configured to cut off the interlabial pad continuous body in a state where the interlabial pad continuous body is folded along the center crease.

8. The apparatus for producing an interlabial pad according to claim 7, wherein the round cut unit comprises a cutter roller comprising a cutter blade.

9. The apparatus for producing an interlabial pad according to claim 1, further comprising a corrugate device comprising a male and a female corrugate mold such that the mini-sheet piece is disposed in between molds so as to be extended.

* * * * *